(12) United States Patent
Lee

(10) Patent No.: US 9,901,536 B2
(45) Date of Patent: Feb. 27, 2018

(54) COMPOSITION FOR IMPROVING SKIN, CONTAINING POMEGRANATE CONCENTRATE AS ACTIVE INGREDIENT

(71) Applicants: HLSCIENCE CO., LTD., Gyeonggi-do (KR); Hae-Yeon Lee, Gyeonggi-do (KR)

(72) Inventor: Hae-Yeon Lee, Gyeonggi-do (KR)

(73) Assignees: HLSCIENCE CO., LTD, Hwaseong-si, Gyeonggi-do (KR); Hae-Yeon Lee, Uiwang-si, Gyeonggi-do (KR)

( * ) Notice: Subject to any disclaimer, the term of this patent is extended or adjusted under 35 U.S.C. 154(b) by 0 days.

(21) Appl. No.: 15/327,845

(22) PCT Filed: Aug. 4, 2014

(86) PCT No.: PCT/KR2014/007174
§ 371 (c)(1),
(2) Date: Jan. 20, 2017

(87) PCT Pub. No.: WO2016/013709
PCT Pub. Date: Jan. 28, 2016

(65) Prior Publication Data
US 2017/0202772 A1    Jul. 20, 2017

(30) Foreign Application Priority Data
Jul. 22, 2014    (KR) .................. 10-2014-0092819

(51) Int. Cl.
| | | |
|---|---|---|
| *A61K 47/00* | (2006.01) | |
| *A61Q 19/02* | (2006.01) | |
| *A61K 36/00* | (2006.01) | |
| *C07C 39/12* | (2006.01) | |
| *A61K 8/97* | (2017.01) | |
| *A23L 33/105* | (2016.01) | |
| *A61K 8/49* | (2006.01) | |
| *A61Q 19/00* | (2006.01) | |
| *A61Q 19/08* | (2006.01) | |

(52) U.S. Cl.
CPC .............. *A61K 8/97* (2013.01); *A23L 33/105* (2016.08); *A61K 8/498* (2013.01); *A61Q 19/007* (2013.01); *A61Q 19/02* (2013.01); *A61Q 19/08* (2013.01); *A23V 2002/00* (2013.01); *A61K 2800/85* (2013.01)

(58) Field of Classification Search
None
See application file for complete search history.

(56) References Cited

U.S. PATENT DOCUMENTS

| | | | |
|---|---|---|---|
| 2006/0269629 A1 | 11/2006 | Bates et al. | |
| 2009/0297681 A1* | 12/2009 | Wilkes | A23L 2/02 426/534 |
| 2012/0263812 A1 | 10/2012 | Commo | |
| 2013/0028994 A1 | 1/2013 | Lee | |

FOREIGN PATENT DOCUMENTS

| | | |
|---|---|---|
| JP | H05331041 A | 12/1993 |
| JP | 2013245170 A | 12/2013 |
| KR | 1020100031839 | 3/2010 |

OTHER PUBLICATIONS

JP2013-245170 machine translation; 15 page pdf; downloaded from Espacenet Aug. 2, 2017.*
Chen et al.; Wound Rep Reg; 1999; 7:79-89.*
Papakonstantinou et al.; Dermato-Endocrinology 4:3, 253-258; Jul.-Dec. 2012.*
Madrigal-Carballo, S. et al., Pomegranate (Punica granatum) supplements: Authenticity, antioxidant and polyphenol composition, Journal of Functional Foods (2009), doi:10.1016/j.jff.2009.02.005.*
Li et al. "A systematic determination of polyphenols constituents and cytotoxic ability in fruit parts of pomegranates derived from five Chinese cultivars" SpringerPlus (2016) 5:914.*
International Search Report in PCT/KR2014/007174 dated Mar. 31, 2015, 6 pages.

* cited by examiner

*Primary Examiner* — Jeffrey T. Palenik
(74) *Attorney, Agent, or Firm* — Goodwin Procter LLP

(57) ABSTRACT

The present disclosure relates to an effect of promoting hyaluronic acid synthesis of a pomegranate concentrate. A pomegranate concentrate, prepared by treating pomegranate with a starch-degrading enzyme and passing the same through a heating concentration process and having an ellagic acid content of 0.8 mg/g or higher and a polyphenol content of 8 mg/g or higher, has an effect of promoting hyaluronic acid. According to the present disclosure, hyaluronic acid synthesis can be promoted and skin moisturization can be improved by administering a food or pharmaceutical composition containing the pomegranate concentrate as an active ingredient to a subject in need of promotion of hyaluronic acid synthesis.

12 Claims, 18 Drawing Sheets

[Fig. 1]
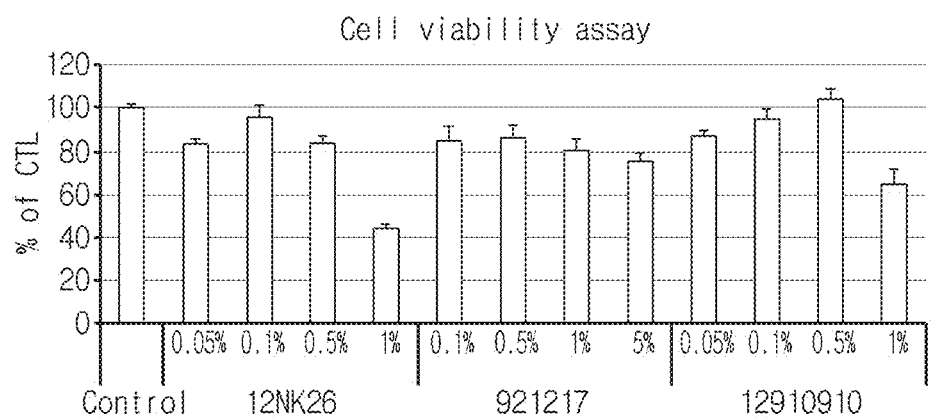
[Fig. 2]
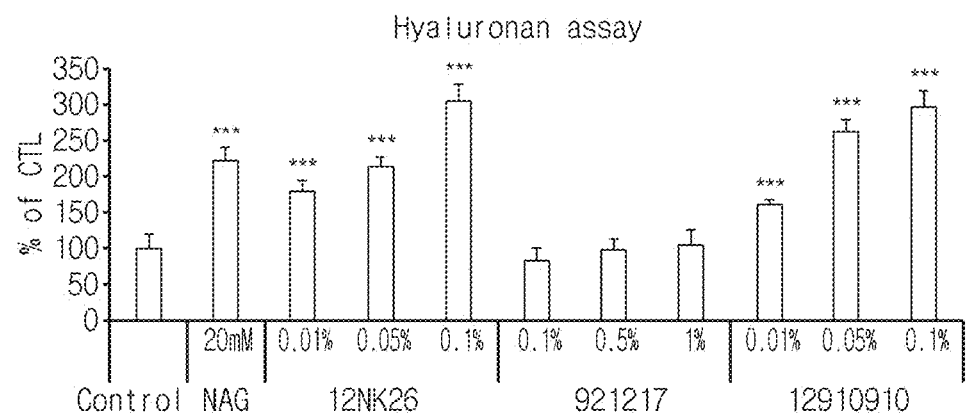

[Fig. 3]
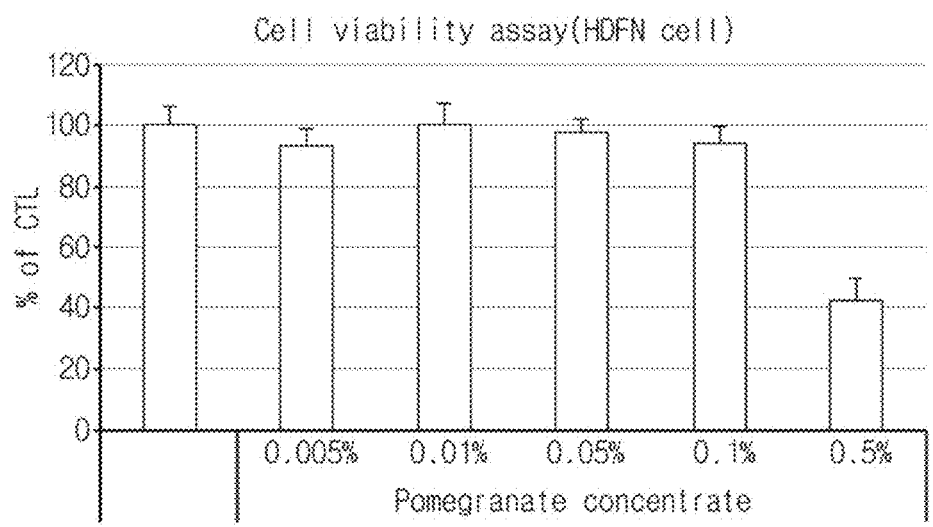
[Fig. 4]
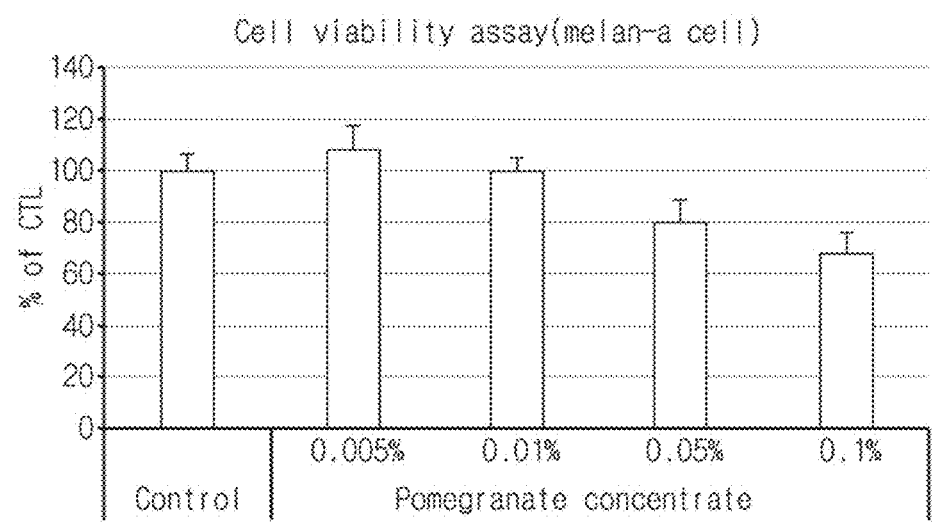

[Fig. 5]
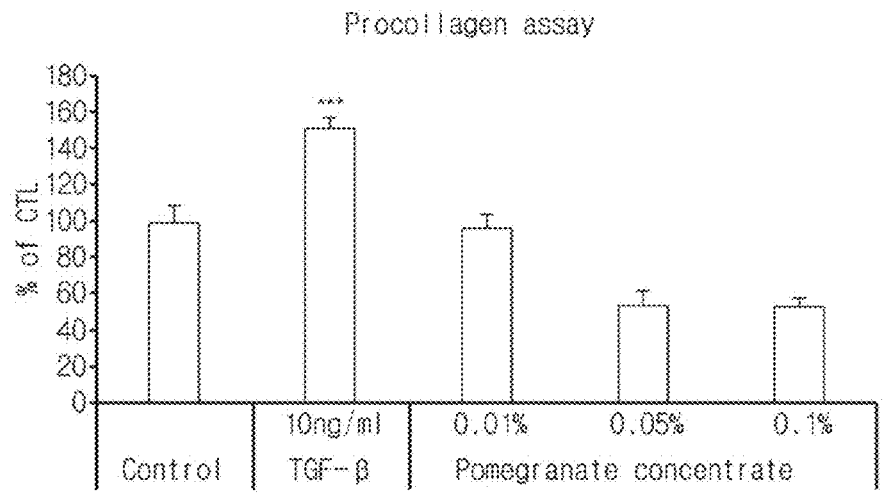
[Fig. 6]
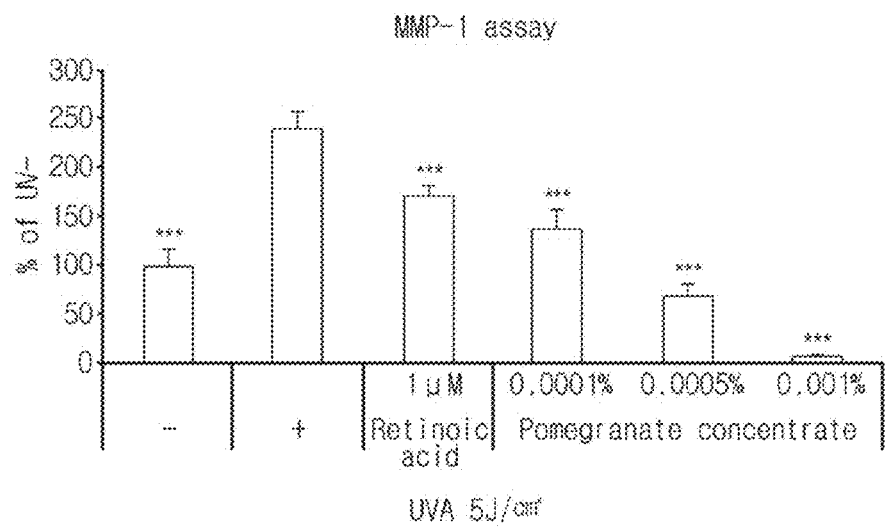

[Fig. 7]
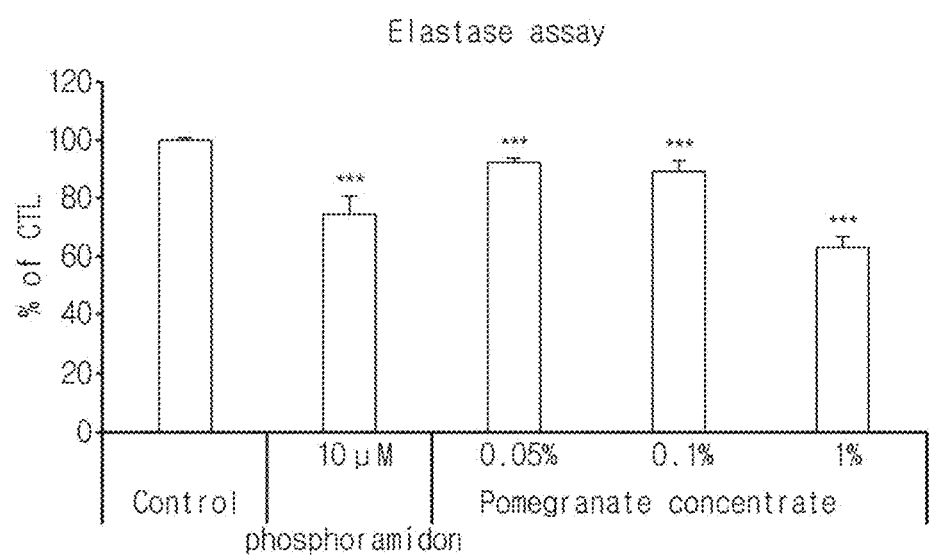

[Fig. 8]
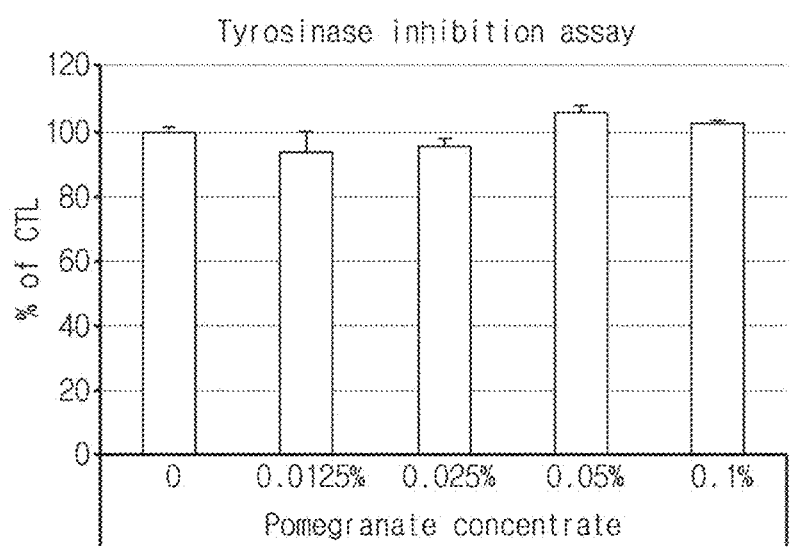
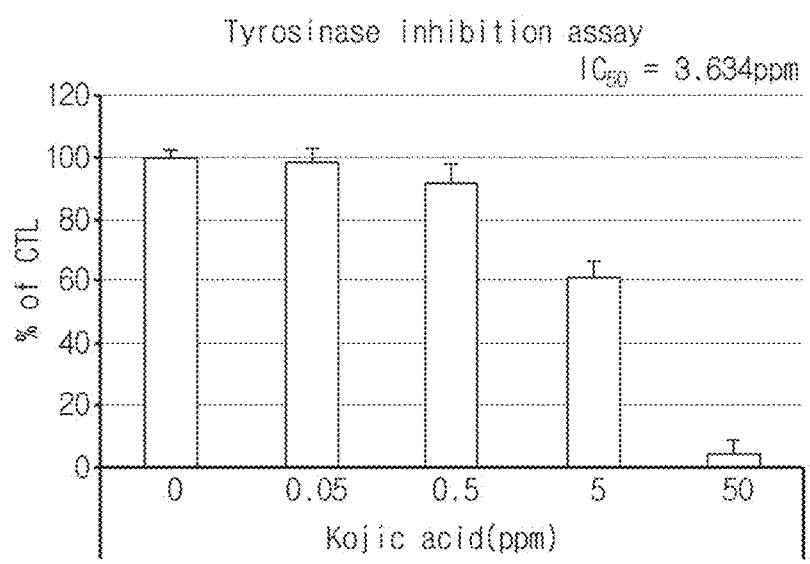

[Fig. 9]
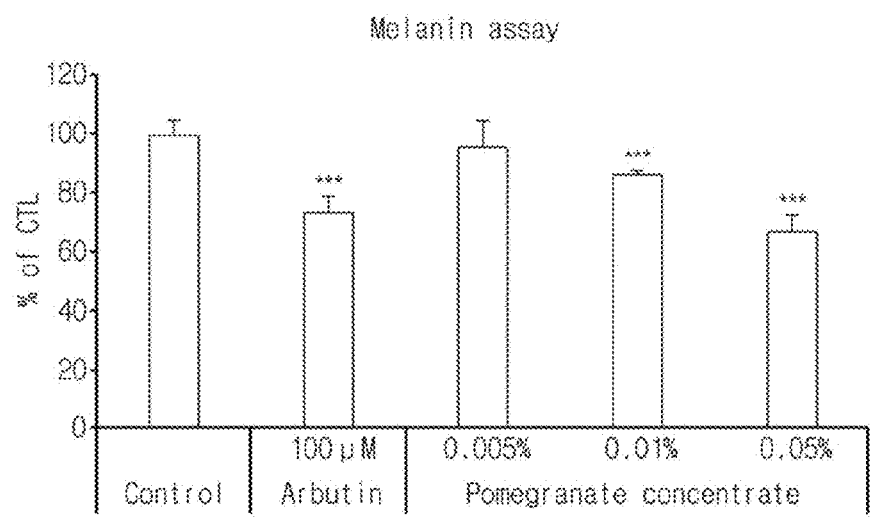
[Fig. 10]
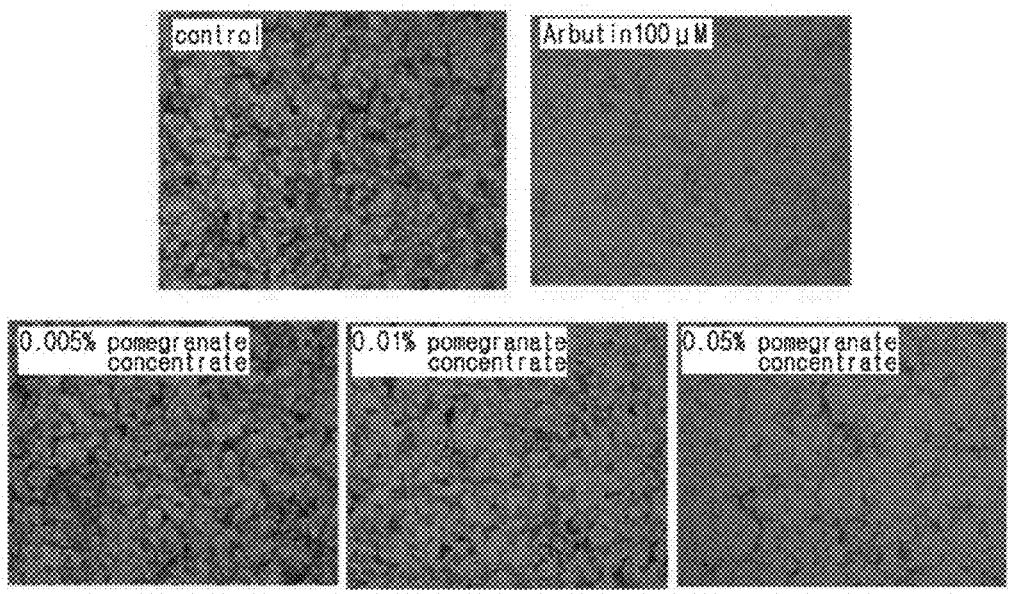

[Fig. 11]
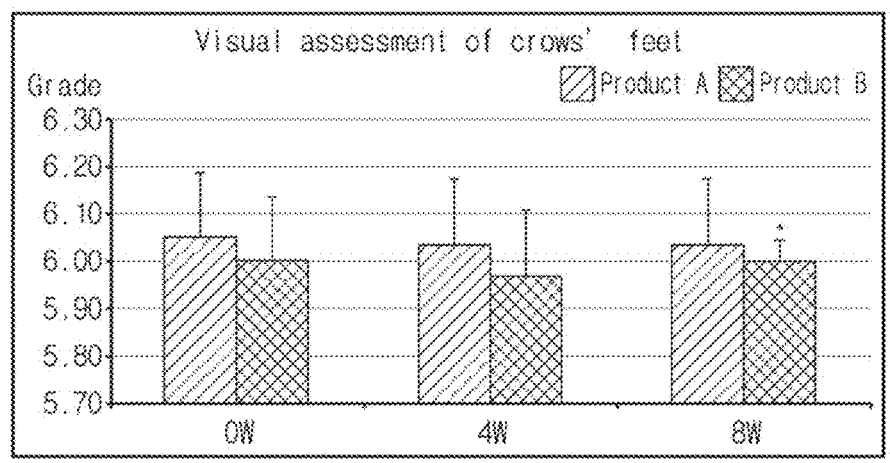
[Fig. 12]
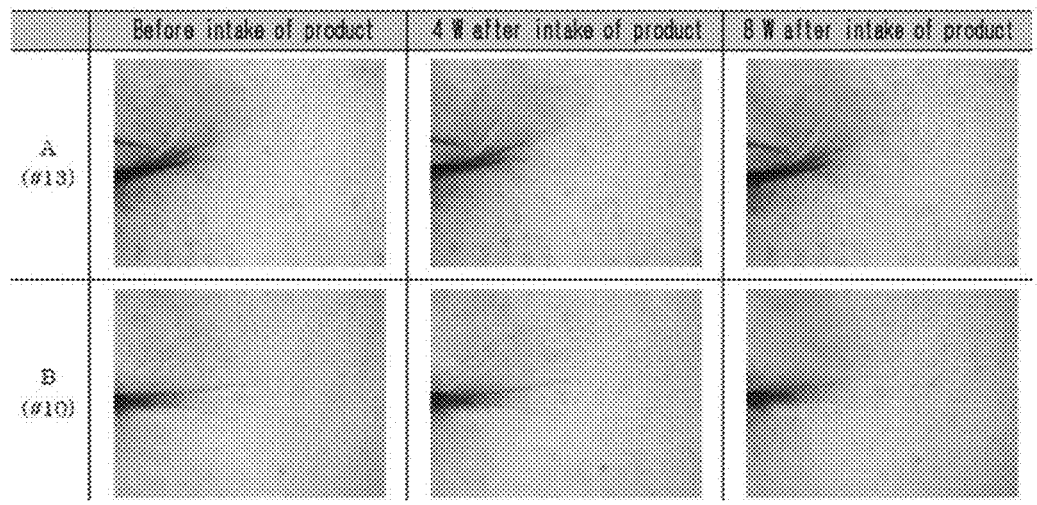

[Fig. 13]
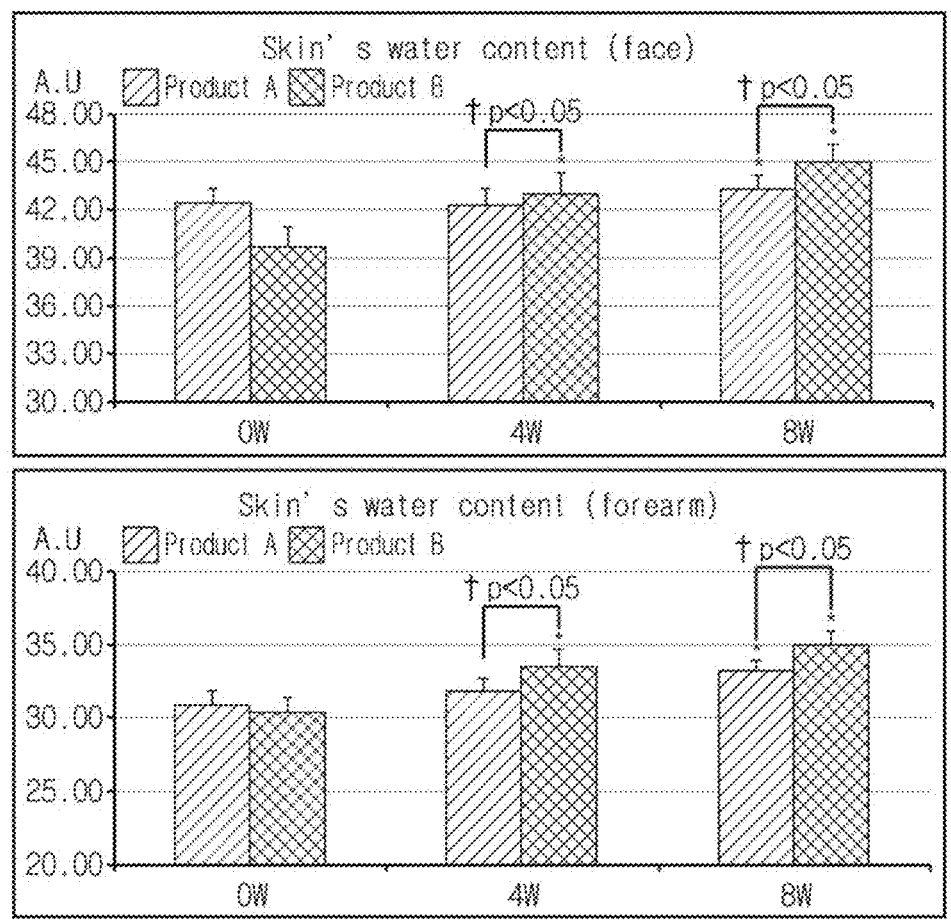

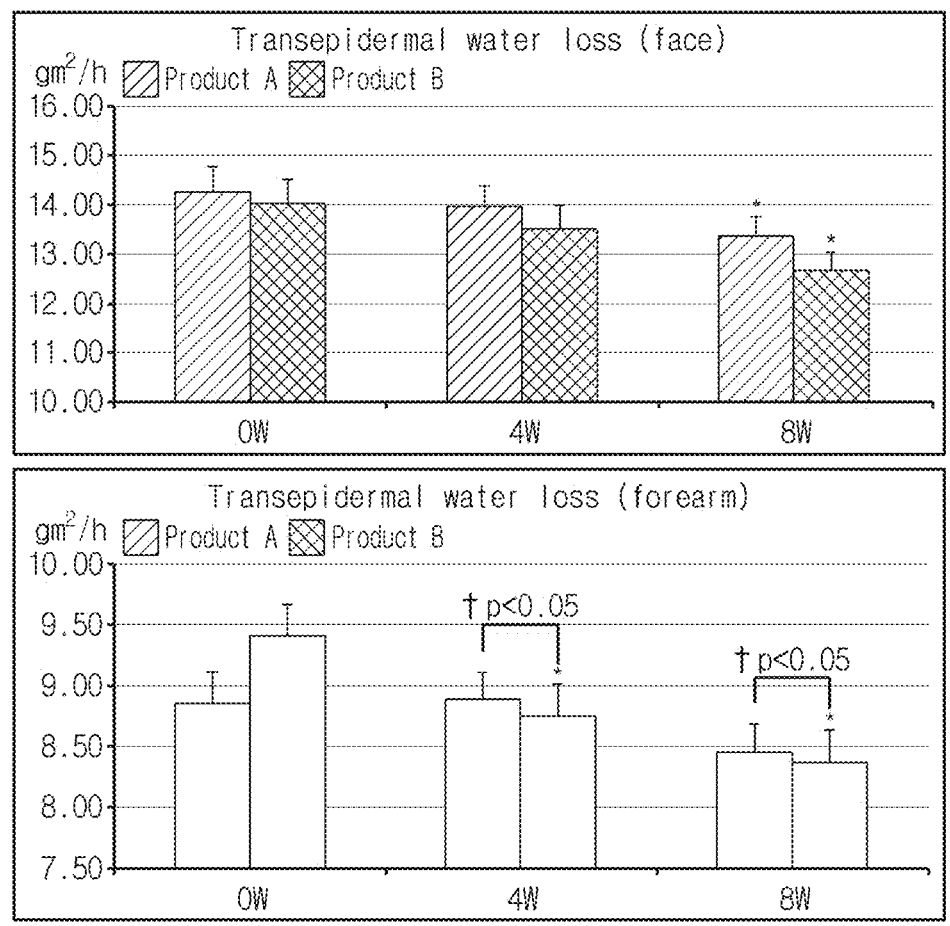
[Fig. 14]

[Fig. 15]
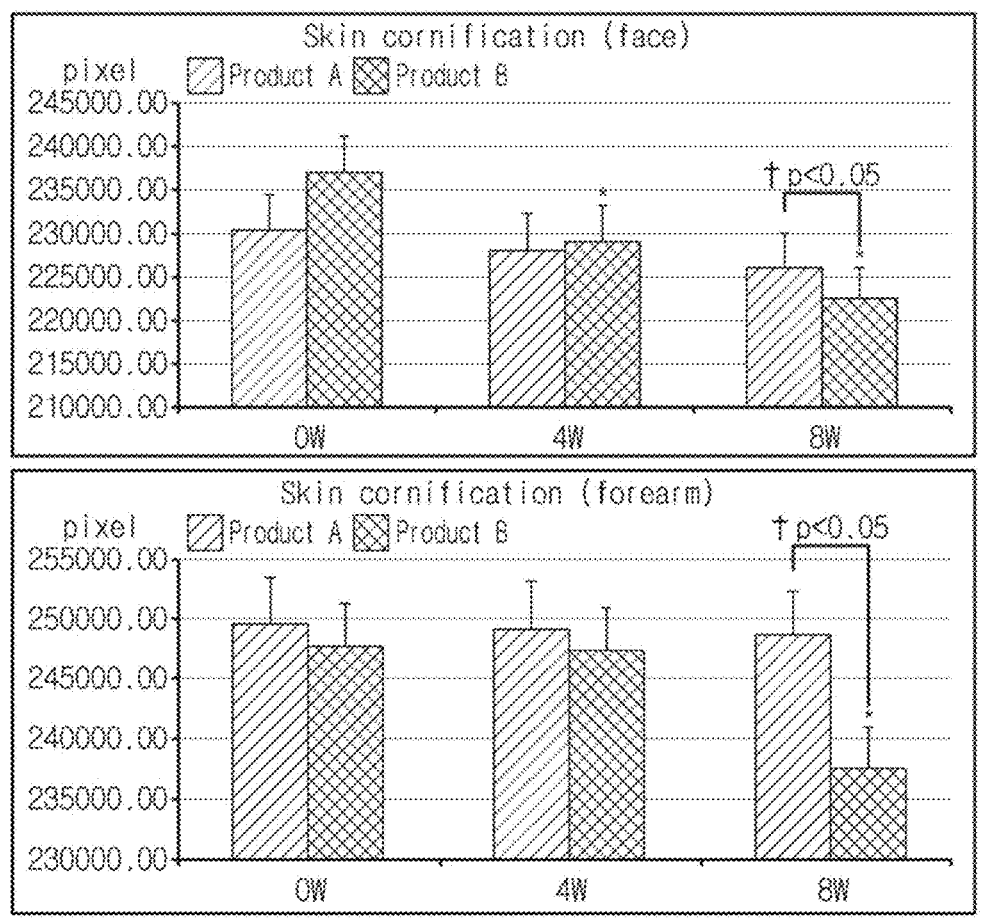

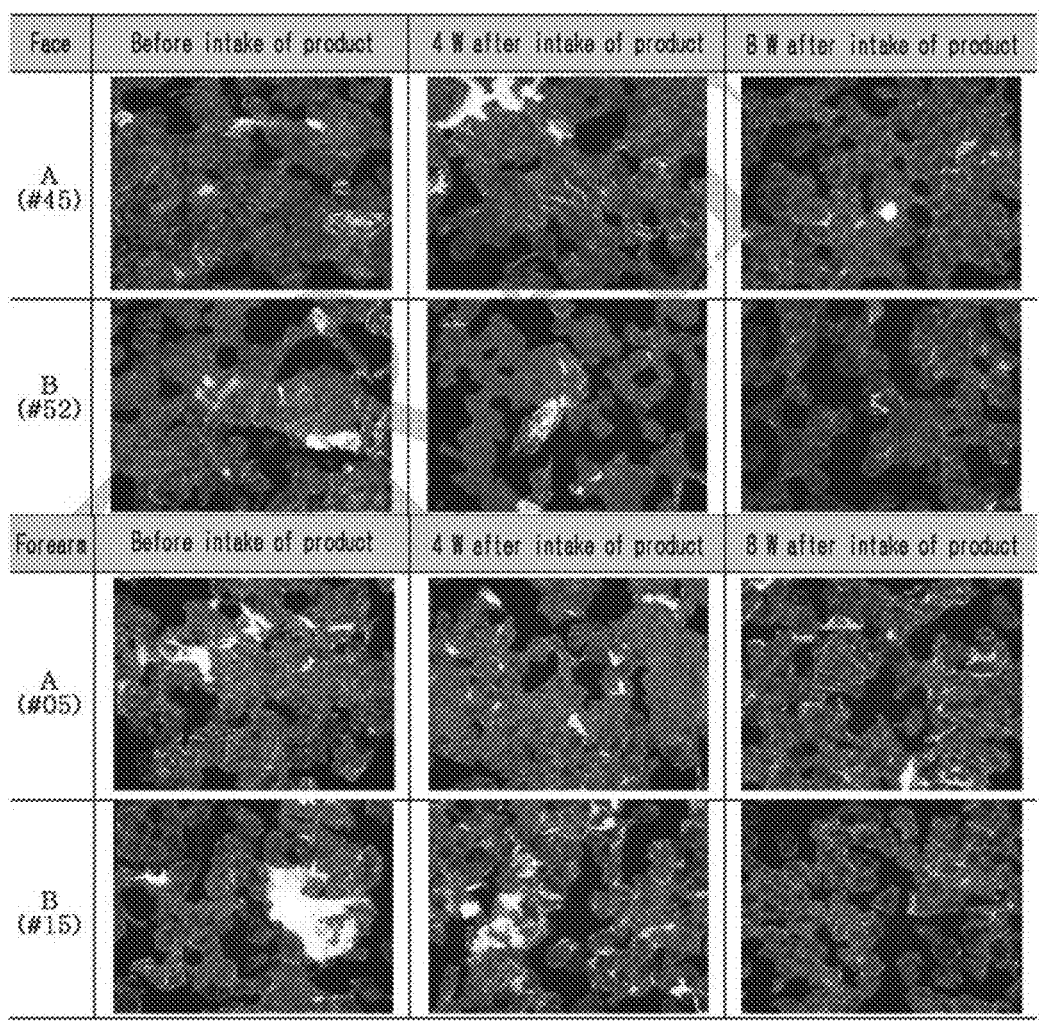
[Fig. 16]

[Fig. 17]
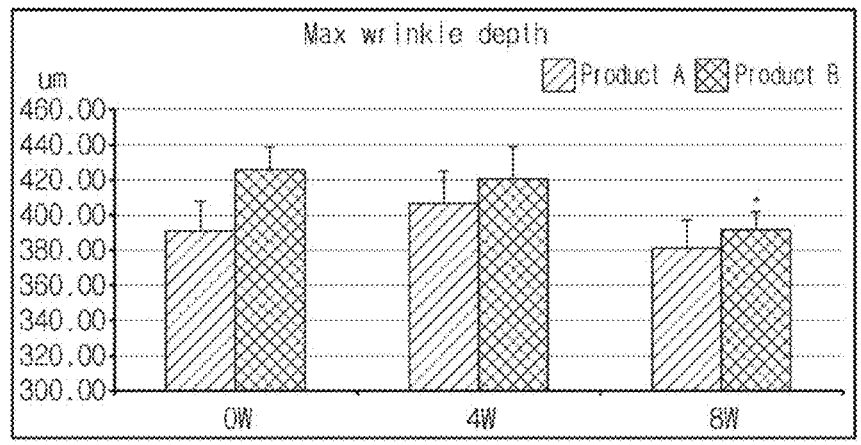
(Mean±SEM, *p<0.05 vs. before application, †p<0.05 vs. control group)
[Fig. 18]
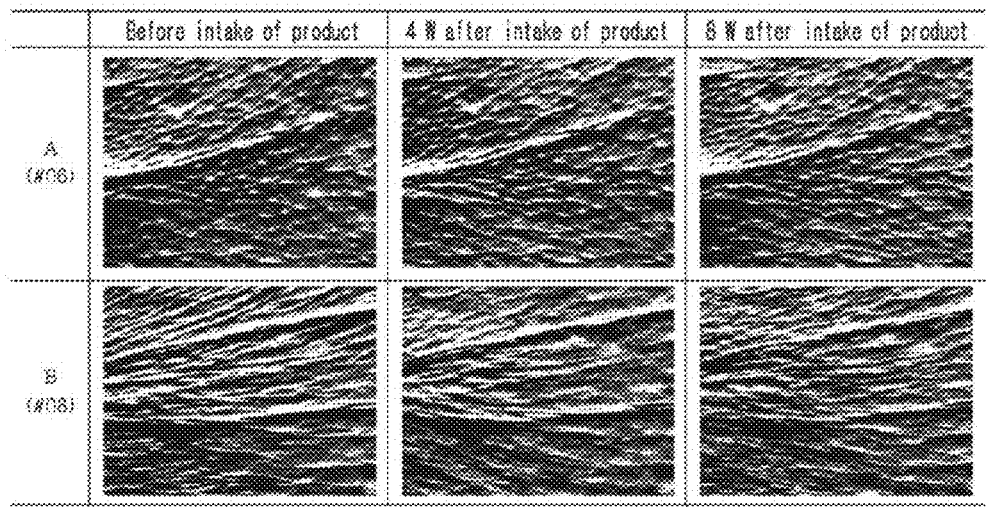

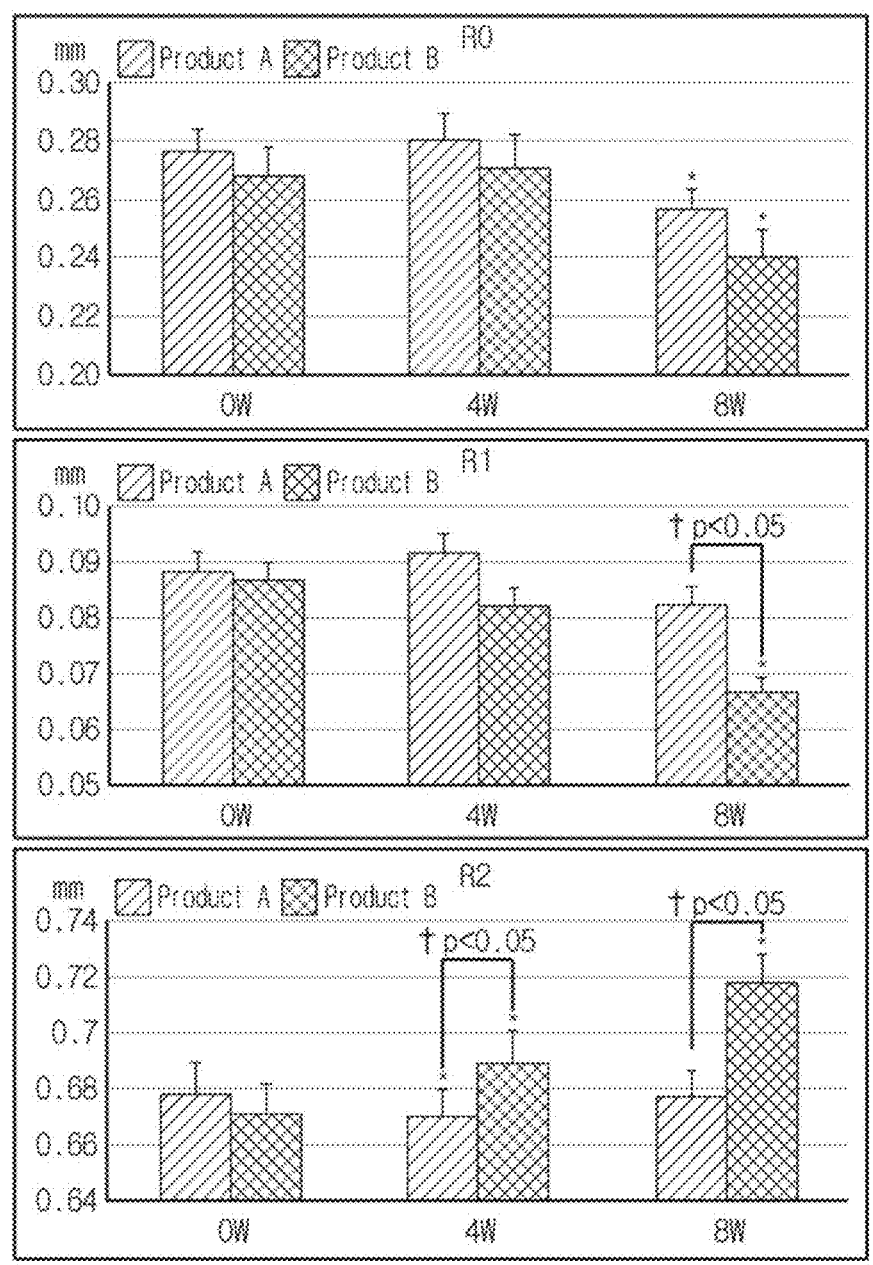
[Fig. 19a]

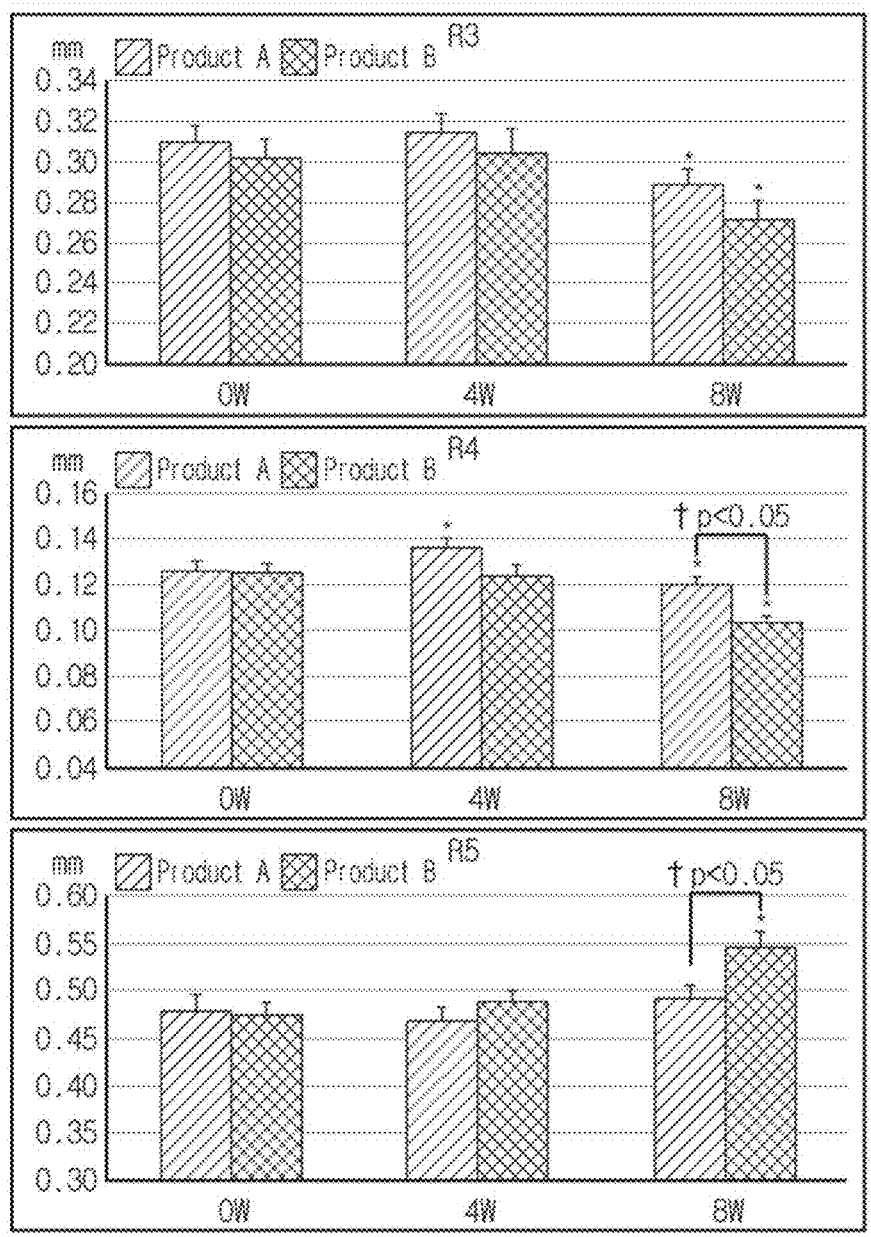

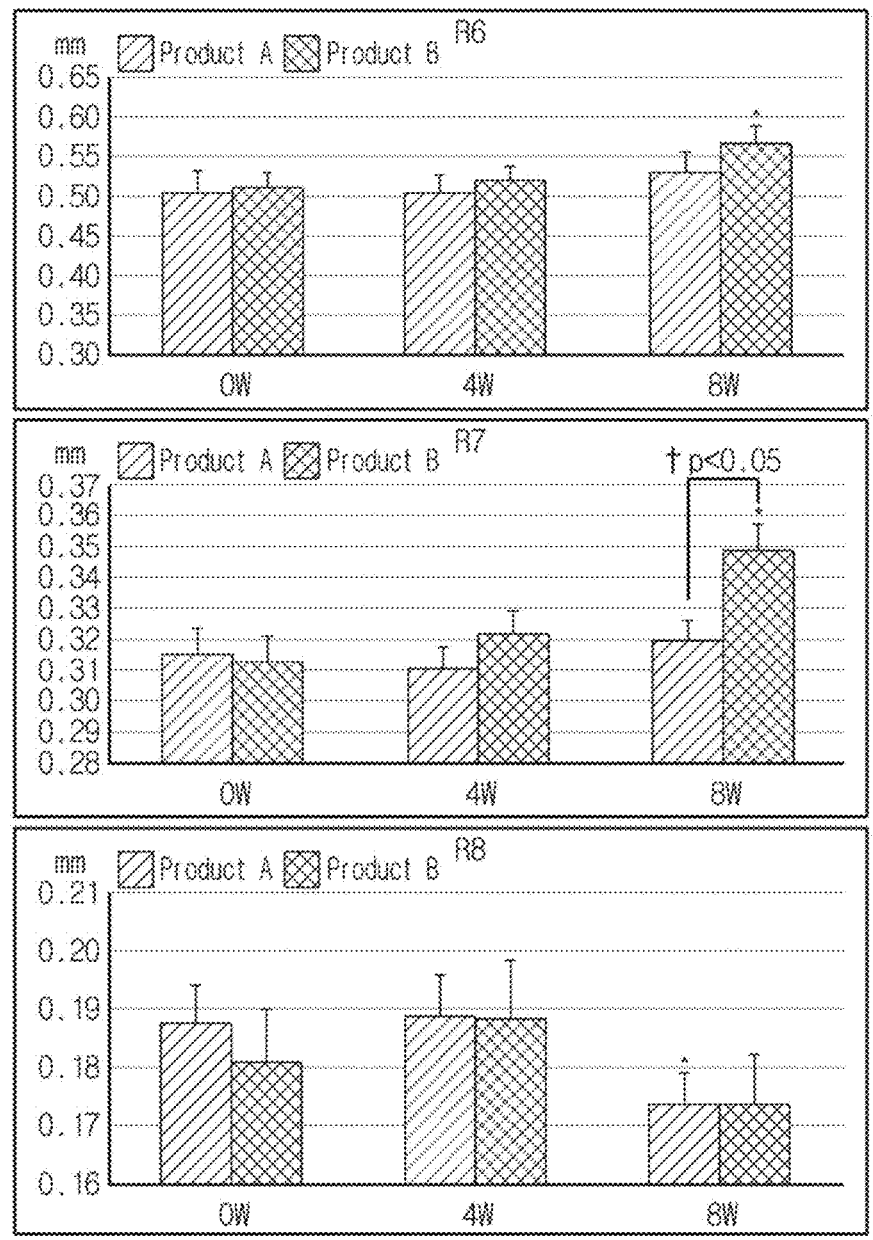
[Fig. 19c]

[Fig. 19d]
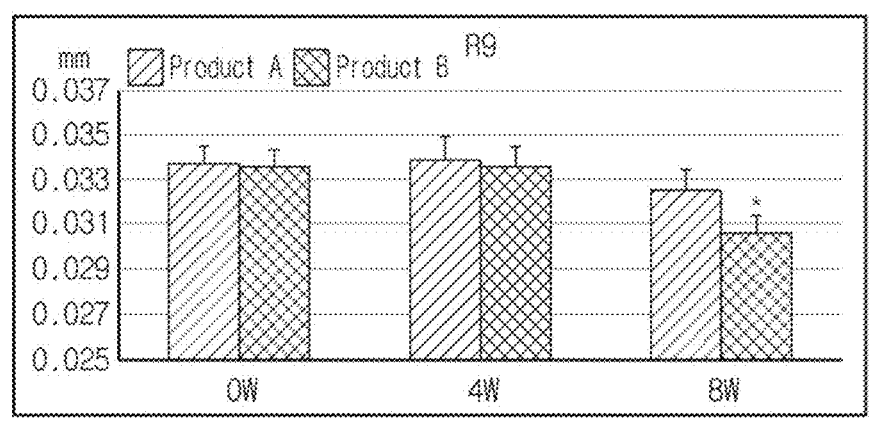
(Mean±SEM, *p<0.05 vs. before application,
†p<0.05 vs. control group)

[Fig. 20]
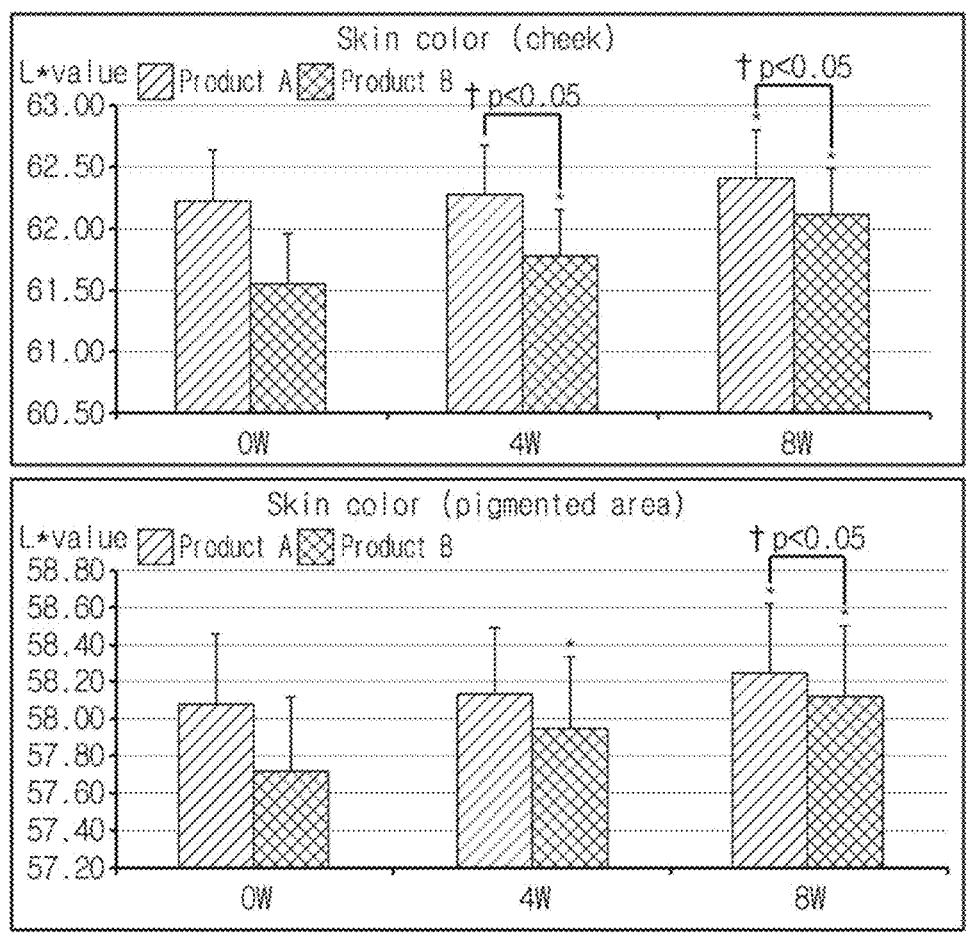

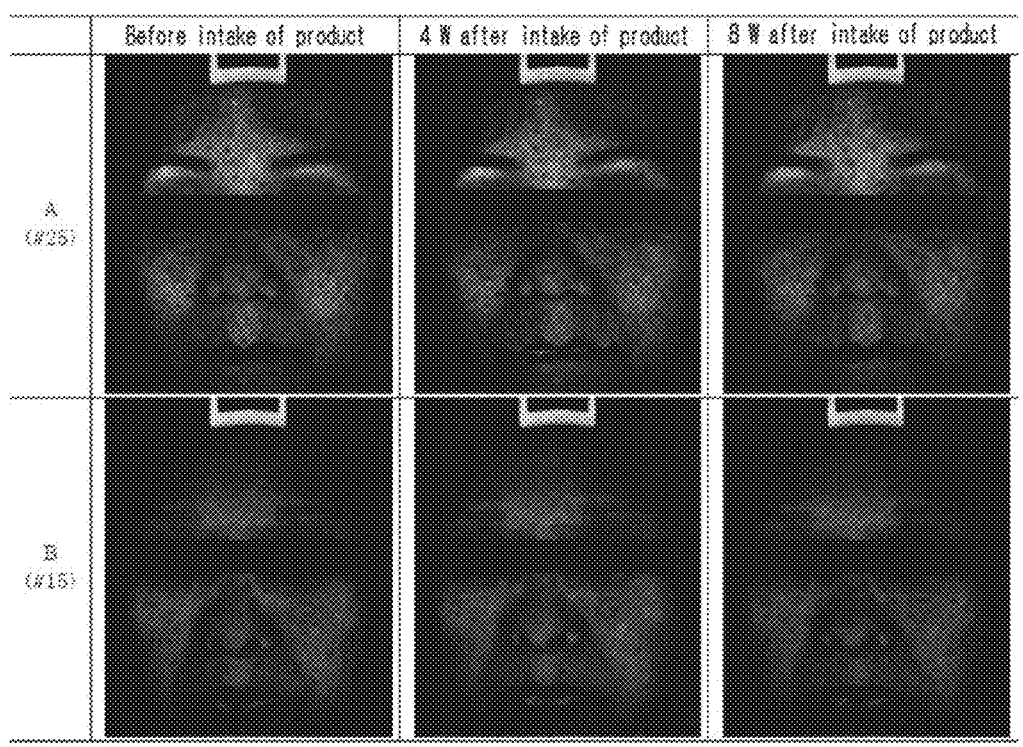
[Fig. 21]

COMPOSITION FOR IMPROVING SKIN, CONTAINING POMEGRANATE CONCENTRATE AS ACTIVE INGREDIENT

CROSS-REFERENCE TO RELATED APPLICATIONS

This non-provisional application is a national stage entry of International Patent Application No. PCT/KR2014/007174, filed Aug. 4, 2014, which claims priority to Korean Patent Application No. 10-2014-0092819, filed Jul. 22, 2014, the entire contents of each of which are hereby incorporated by reference.

TECHNICAL FIELD

This application claims the priority of Korean Patent Application No. 10-2014-0092819, filed on Jul. 22, 2014, the disclosure of which is incorporated herein by reference in its entirety.

The present disclosure relates to a method for promoting hyaluronic acid synthesis and, thereby, improving skin moisturization, skin wrinkles, skin whitening, skin cornification, etc., using a natural plant material as an active ingredient.

BACKGROUND ART

Hyaluronic acid is a biologically synthesized natural substance abundant in the skin, etc, of animals, Hyaluronic acid is also called hyaluronan. It is hydrophilic because it has many hydroxyl (—OH) groups and is involved in skin moisturization. It also regulates various physiological actions by reacting with the CD44 protein expressed in various epithelial cells.

Skin is an organ which is constantly in contact with outside. It is composed of three layers of the epidermis, the dermis and the subcutaneous tissue from outside and protects the human body from physical and/or chemical stimuli from outside. Especially, the skin plays an important role of controlling loss of water, which accounts for about 65-70% of the human body, transports various physiologically active substances necessary for the human body and maintains soft and moist states, out of the human body.

However, with aging, the skin intrinsically experiences decreased secretion of various hormones regulating metabolism as well as decreased biosynthesis of immunoproteins and biological proteins necessary for the body due to decreased function of immune cells and cellular activity. Extrinsically, due to increased UV radiation caused by the destruction of the ozone layer and aggravated environmental pollution, the function and aesthetic beauty of the skin decline owing to increase in free radicals, harmful reactive oxygen species, etc.

Therefore, researches are being actively carried out on substances with superior efficacy for improving skin and safety. In addition, researches are being actively carried out on substances which improve skin condition through external application such as cosmetics and provide skin-improving effect through dietary intake.

In this regard, interests are consistently increasing in natural plant materials exhibiting skin-improving effect. Because many natural plant materials have shown proven safety or effect throughout use for hundreds of years, they are advantageous in terms of safety and environment friendliness.

Accordingly, there is a need for a substance which is effective in improving skin and is safe.

DISCLOSURE

Technical Problem

The present disclosure is directed to providing a natural plant material which is effective in promoting hyaluronic acid synthesis.

The present disclosure is also directed to providing a composition for improving skin, particularly moisturizing skin, which contains a natural plant material effective for hyaluronic acid synthesis as an active ingredient, and a method for improving skin, particularly moisturizing skin, using the same.

The present disclosure is also directed to providing a method for processing a natural plant material composition which improves the effect of promoting hyaluronic acid synthesis.

Technical Solution

In an aspect, the present disclosure provides: a method for promoting hyaluronic acid synthesis, which includes administering a food or pharmaceutical composition containing a pomegranate concentrate as an active ingredient to a subject in need of promotion of hyaluronic acid synthesis; and/or a composition for promoting hyaluronic acid synthesis, which contains a pomegranate concentrate as an active ingredient.

The pomegranate concentrate may contain specifically 0.8 mg/g or more, more specifically 0.8-3 mg/g, of ellagic acid.

Also, pomegranate concentrate may contain specifically 8 mg/g or more, more specifically 8-15 mg/g, of polyphenol.

The inventors of the present disclosure have found out surprisingly that a pomegranate concentrate prepared through a process of concentrating a pomegranate degradation product obtained by treating a pomegranate fruit with a starch-degrading enzyme by heating is effective in promoting hyaluronic acid synthesis and that a composition containing the pomegranate concentrate as an active ingredient exhibits excellent skin-moisturizing effect. They have also found out that the pomegranate concentrate exhibits, along with the skin-moisturizing effect, superior effect of improving skin, including improving skin elasticity, improving pigmentation, whitening skin, improving skin tightening, improving skin texture, brightening skin tone and/or reducing skin cornification.

Pomegranate (*Punica granatum* L.) is a plant native to Southwestern Asia, northwestern India and California. It is widely distributed in subtropical and tropical regions. From long ago, pomegranate, especially red pomegranate, has been known as an invigorant and also has been known to be effective in preventing hypertension and arteriosclerosis. It is rich in water-soluble sugars at 38-47% and also contains various vitamins and minerals.

The pomegranate concentrate according to the present disclosure refers to one prepared through a process concentrating a pomegranate degradation product obtained by treating a pomegranate fruit with a starch-degrading enzyme by heating.

The treatment with the starch-degrading enzyme may be performed specifically at 40-65° C., more specifically at 45-60° C. The treatment with the starch-degrading enzyme may be performed specifically within 100 minutes, more specifically for 50-70 minutes, most specifically for about 60 minutes.

The concentrating by heating may be performed specifically for 3 or more times, more specifically at 40-110° C. for 3 or more times.

The pomegranate concentrate may contain 0.8 mg or more, specifically 0.8-3 mg, more specifically 1.8-3 mg/g, even more specifically 2.4-3 mg/g, most specifically 2.7-3 mg/g, of ellagic acid although the content may vary depending on where and when the pomegranate is harvested. Also, the pomegranate concentrate may contain 8 mg/g or more, specifically 8-15 mg/g, more specifically 11.5-13 mg/g, even more specifically 11.79-12.59 mg/g, of polyphenol. When the ellagic acid concentration is below 0.8 mg/g or when the polyphenol concentration is below 8 mg/g, the effect of promoting hyaluronic acid synthesis may be insignificant. And, when the ellagic acid concentration exceeds 3 mg/g or when the polyphenol concentration exceeds 15 mg/g, side effects such as the liver enzyme levels of GOT and GPT deviating from normal ranges may occur.

It is thought that the effect of promoting hyaluronic acid synthesis of the pomegranate concentrate is derived from a specific preparation method, in particular, from treatment with a starch-degrading enzyme, concentration of the pomegranate concentrate, heating temperature and pressure, etc., although not being limited thereto. More specifically, a pomegranate concentrate obtained by compressing a pomegranate fruit, treating with a starch-degrading enzyme and then concentrating by heating has a remarkably superior effect of promoting hyaluronic acid synthesis as compared to a pomegranate juice obtained by compressing a pomegranate fruit. It is though that various sugars or repeating units present in the natural pomegranate fruit are converted to aglycons during the treatment with a starch-degrading enzyme and/or heating concentration, although the present disclosure is not limited thereto. For instance, the pomegranate concentrate according to the present disclosure contains polyphenols in remarkably higher amounts than the pomegranate juice of the same degree of concentration.

The pomegranate used in the present disclosure may be, for example, Iranian pomegranate, Turkish pomegranate, American pomegranate or a mixture thereof. For example, Turkish pomegranate cultivars include Hicaznar pomegranate cv., Cekirdeksiz VI pomegranate cv., Silifke Asisi pomegranate cv., Katirbasi pomegranate cv., Lefan pomegranate cv., etc., although not being limited thereto.

For preparation of the pomegranate concentrate according to the present disclosure, only a pomegranate pulp excluding the pomegranate pericarp and seed may be used. The pericarp and seed of pomegranate may cause side effects. For example, alkaloids contained in the pomegranate pericarp may decline biological functions and have the risks of spasm, convulsion, stupor, etc. because they affect the respiratory system and muscles. And, the pomegranate seed concentrate may cause side effects such as allergy, tongue swelling, etc. in some people.

In another aspect, the present disclosure provides a method for preparing a pomegranate concentrate capable of promoting hyaluronic acid synthesis, which includes a step of treating a pomegranate fruit with a starch-degrading enzyme and a step of concentrating a pomegranate degradation product by heating.

The pomegranate concentrate according to the present disclosure may be prepared by a method including a step of treating a pomegranate fruit with a starch-degrading enzyme and a step of concentrating a pomegranate degradation product by heating. For example, pomegranate is washed and sterilized in short time after completely removing the pericarp and seed. Then, polysaccharides such as starch, etc. contained in pomegranate are degraded by adding a starch-degrading enzyme. Then, a pomegranate concentrate may be prepared by optionally controlling the turbidity, color, viscosity etc. of the pomegranate concentrate by adding an additive such as gelatin, silicon dioxide, bentonite, silica sol, tannin, cellulose, calcium caseinate, etc. and then concentrating the same by heating. In addition, a filtration step may be included between the individual steps. For example, a filtration step may be included after the step of removing the pericarp and seed and before the step of sterilizing at high temperature, after the step of treating with the starch-degrading enzyme and before the concentration step and/or after the concentration step.

More specifically, a step of obtaining a pomegranate degradation product by treating a pomegranate fruit with the starch-degrading enzyme may include the following steps:

S1) a step of removing the pericarp and seed from Iranian pomegranate, Turkish pomegranate, American pomegranate or a mixture thereof and obtaining only the pomegranate pulp In an exemplary embodiment, a concentrate of a pomegranate pulp only excluding the pomegranate pericarp and seed is used.

S2) a step of sterilizing the pomegranate pulp

The pomegranate pulp is sterilized. The sterilization may be performed at high temperature or low temperature and it is desired that the sterilization is performed in short time (e.g., 50-80 seconds).

S3) a step of treating the sterilized pomegranate pulp with a starch-degrading enzyme The sterilized pomegranate pulp is treated with a starch-degrading enzyme. The starch-degrading enzyme may be treated specifically at 40-65° C., more specifically at 45-60° C. The treatment may be performed specifically within 100 minutes, more specifically for 50-70 minutes, even more specifically within 60 minutes, most specifically for about 60 minutes. Various starch-degrading enzymes known in the art may be used without particular limitation. For example, pectinase, proteinase, amylase, cellulase, etc. may be used. Specifically, pectinase may be used.

The pomegranate degradation product may be concentrated by heating at 40-110° C. specifically for 3 or more times. More specifically, the heating concentration may be performed by two methods as described below:

S4-1) The pomegranate pulp degradation product may be concentrated by heating at 70-100° C. and 400-850 mbar for 2 or more times and then at 40-80° C. and 100-350 mbar for 1 or more time.

That is to say, the pomegranate pulp degradation is concentrated by heating at high temperature under elevated pressure and then at low pressure under reduced pressure.

The heating concentration at high temperature under elevated pressure may be performed specifically for 2 or more times, more specifically for 3 or more times, and the heating concentration at low pressure under reduced pressure may be performed specifically for 1 or more time, more specifically for 2 or more times. The heating concentration pressure may be performed for a total of 3 or more times.

The heating concentration at high temperature under elevated pressure is performed at 70-100° C. and 400-850 mbar and is not specially limited in detailed method. Specifically, it may be performed by performing first heating concentration at 70-85° C. and 400-550 mbar, second heating concentration at 85-92° C. and 550-750 mbar and third heating concentration at 92-100° C. and 750-850 mbar. More specifically, it may be performed by performing first heating concentration at 78-82° C. and 450-500 mbar, second heating concentration at 85-90° C. and 600-650 mbar and third heating concentration at 92-98° C. and 800-850 mbar.

The heating concentration at low temperature reduced elevated pressure is performed at 40-80° C. and 100-350 mbar and is not specially limited in detailed method. Specifically, it may be performed by performing fourth heating concentration at 60-80° C. and 250-350 mbar and fifth heating concentration at 40-60° C. and 100-250 mbar. More specifically, it may be performed by performing fourth heating concentration at 65-72° C. and 300-330 mbar and fifth heating concentration at 45-55° C. and 100-150 mbar.

S4-2) The pomegranate pulp degradation product may be concentrated by performing first heating concentration at 55-90° C., second heating concentration at 105-110° C. and third heating concentration at 100-105° C.

In an exemplary embodiment, the pomegranate concentrate according to the present disclosure is effective in promoting hyaluronic acid synthesis. Accordingly, an advantageous physiological effect resulting from increased hyaluronic acid synthesis may be expected. For example, it is effective in improving skin moisturization.

Therefore, in an aspect, the present disclosure may provide a method for improving skin moisturization and/or a composition for moisturizing skin. More specifically, the present disclosure may provide a composition for moisturizing skin, which contains a pomegranate concentrate as an active ingredient. In another aspect, the present disclosure may provide a method for improving skin moisturization, which includes a step of administering a food or pharmaceutical composition containing a pomegranate concentrate as an active ingredient to a subject in need of skin moisturization.

In another aspect, the present disclosure may provide a method for promoting hyaluronic acid synthesis by treating isolated cells with a composition containing a pomegranate concentrate as an active ingredient in vitro.

For example, the subject may be an animal including a rodent, a mammal, etc., specifically a human.

And, the cell may be one derived from an animal such as a rodent, a mammal, etc. Specifically, it may be derived from a human.

The inventors of the present disclosure have also found out that the pomegranate concentrate is effective in improving skin wrinkles by decreasing MMP-1 and elastase in a concentration-dependent manner and in whitening skin by decreasing melanin in a concentration-dependent manner, in addition to the effect of promoting hyaluronic acid synthesis as described above. It was also found out through clinical evaluation that it has excellent effect of improving skin, including reducing cornification, improving skin elasticity, improving skin color, improving skin wrinkles, whitening skin, etc.

Therefore, the composition containing a pomegranate concentrate as an active ingredient according to the present disclosure may be used to improve skin, including skin moisturization. For example, it may be used to provide one or more skin-improving effect selected from a group consisting of improving skin elasticity, improving pigmentation, whitening skin, improving skin tightening, improving skin texture, brightening skin tone and/or reducing cornification, specifically one or more selected from a group consisting of improving skin wrinkles, whitening skin, improving skin elasticity and reducing cornification, in addition to moisturizing skin.

The composition according to the present disclosure may be administered either after the symptoms of hyaluronic acid deficiency and/or insufficient skin moisturization have occurred or in advance when the symptoms of hyaluronic acid deficiency and/or insufficient skin moisturization are expected or diagnosed.

The composition according to the present disclosure may be used for various purposes when the above-described effects are desired. For example, it may be used as a food (including health functional food) composition, a pharmaceutical composition or a cosmetic composition.

Accordingly, the present disclosure provides a food composition, a pharmaceutical composition or a cosmetic composition containing the composition described above. More specifically, the present disclosure may provide a food composition, a pharmaceutical composition or a cosmetic composition for skin moisturization effective in promoting hyaluronic acid synthesis, which contains a pomegranate concentrate prepared by the method described above as an active ingredient.

The food includes a supplementary health food, a health functional food, a functional food, etc., although not being limited thereto, and may further include a natural food, a processed food, a foodstuff, etc. to which the pomegranate concentrate according to the present disclosure is added.

The food composition according to the present disclosure may contain, in addition to the pomegranate concentrate, ingredients commonly used in foods or food compositions. Natural plant concentrates, e.g., paeoniae radix, corni fructus, acanthopanacis cortex, lingzhi mushroom, *Aurantii nobilis* pericarpium, eucomia cortex, *Angelica sinensis* radix, gardeniae fructus, astragali radix, malt and trifoliate orange, and vitamin C, fructooligosaccharide, stevioside, purified water, maltodextrin, etc. may be further included alone or in combination within ranges not negatively affecting the purpose of the present disclosure. However, other active ingredients and/or additives that can be further added to the food of the present disclosure are not limited to the examples described above. For example, the food according to the present disclosure may contain water-soluble vitamins such as thiamine (vitamin $B_1$), riboflavin, ascorbic acid, niacin and vitamin $B_6$, fatty acids such as myristic acid, palmitic acid, stearic acid, oleic acid, linoleic acid, etc., weak acids such as glycolic acid and acetic acid, and amino acids including threonine, valine, methionine, isoleucine, leucine, phenylalanine, tryptophan and lysine as 8 essential amino acids as well as aspartic acid, serine, glutamic acid, proline, glycine, alanine, cysteine, tyrosine, histidine, arginine, etc. The mixing amount of the active ingredient may be determined adequately depending on the purpose of use (prevention, improvement, therapeutic treatment, etc.). In general, the food composition according to the present disclosure may contain 10-90 wt % of the active ingredient for a food or a drink. The effective dose of the pomegranate concentrate in the food composition may be determined in accordance with the effective dose of a pharmaceutical composition and may be lower than the above range for long-term intake. But, because the active ingredient has no safety problem at all, it can be used in larger amounts.

The kind of the food according to the present disclosure is not specially limited. For example, it may be in the form of a formulation for administration such as a tablet, a hard or soft capsule, a solution, a suspension, etc. These formulations may be prepared by using a common acceptable carrier. For example, a formulation for oral administration may be prepared by using an excipient, a binder, a disintegrant, a lubricant, a sol bilizer, a suspending agent, a preservative, an extender, etc.

The type of the food according to the present disclosure is not specially limited. For example, it may be in the form of a fortified food, a dietary supplement, a non-alcoholic drink, a sports drink, a fruit drink, a tea- or milk-based drink, or a liquid food, although not being limited thereto.

The pharmaceutical composition according to the present disclosure may be administered orally or parenterally and may be in the form of a general medicinal formulation. Specific pharmaceutical formulations include formulations for oral administration such as a tablet, a hard or soft capsule, a solution, a suspension, etc. These formulations may be prepared by using a common acceptable carrier. For example, a formulation for oral administration may be prepared by using an excipient, a binder, a disintegrant, a lubricant, a solubilizer, a suspending agent, a preservative, an extender, etc.

The administration dosage of the pharmaceutical composition containing the pomegranate concentrate as an active ingredient according to the present disclosure may be determined by an expert in consideration of various factors such as the physiological condition, age and sex of a patient, the presence of a complication, etc. In general, a dosage of 0.1-10 mg, specifically 10 mg to 1 g, per kg body weight may be administered for an adult. A unit dose may contain the daily dosage of the pharmaceutical composition or 1/2, 1/3, 1/4, 1/5, 1/6, 1/7 1/8, 1/9 or 1/10 thereof and may be administered 1-10 times a day. The administration dosage may be less than the above range for long-term intake and, because the active ingredient has no safety problem at all, it can be used in larger amounts. In an exemplary embodiment, health-related indices (e.g., red blood cell (RBC) count, blood urea nitrogen (BUN) level, aspartate aminotransferase (AST) level, alanine aminotransferase (ALT) level, creatine level, glucose level, S-G level, etc.) are maintained within normal ranges even after the pomegranate concentrate according to the present disclosure is taken at a dosage of 10 mL/day. Accordingly, the effect of promoting hyaluronic acid synthesis and/or improving skin including moisturizing skin can be achieved safely without side effects on the body.

Advantageous Effects

In accordance with the present disclosure, the effect of promoting hyaluronic acid synthesis can be expected by using a pomegranate concentrate. In addition, an excellent skin-moisturizing effect and the superior effect of improving skin wrinkles, whitening skin, reducing cornification, etc. can be expected.

BRIEF DESCRIPTION OF DRAWINGS

FIG. 1 shows a toxicity test result of a pomegranate concentrate for HaCaT cells.

FIG. 2 shows a result of evaluating the skin-moisturizing effect of a pomegranate concentrate by measuring hyaluronan production (*$p<0.05$, $p<0.01$, *$p<0.005$).

FIG. 3 shows a toxicity test result of a pomegranate concentrate for HDF-N cells.

FIG. 4 shows a toxicity test result of a pomegranate concentrate for Melan-a cells.

FIG. 5 shows a result of evaluating the wrinkle-improving effect by measuring procollagen synthesis (*$p<0.05$, $p<0.01$, *$p<0.005$).

FIG. 6 shows a result of evaluating the wrinkle-improving effect by measuring MMP-1 inhibition (*$p<0.05$, $p<0.01$, *$p<0.005$).

FIG. 7 shows a result of evaluating the wrinkle-improving effect by measuring elastase inhibition (*$p<0.05$, $p<0.01$, $p<0.005$).

FIG. 8 shows a result of evaluating the skin-whitening effect by analyzing tyrosinase inhibition activity.

FIG. 9 shows a result of evaluating the skin-whitening effect by measuring inhibition of melanin synthesis.

FIG. 10 shows a result of observing melanocytes through a melanin synthesis inhibition assay.

FIG. 11 shows a result of visual assessment of crows' feet with time.

FIG. 12 shows the change in crows' feet of subjects before and after intake of products.

FIG. 13 shows the change in skin's water content with time after application of products.

FIG. 14 shows the change in transepidermal water loss after application of products.

FIG. 15 shows the change in skin cornification with time after application of products.

FIG. 16 shows the change in skin cornification on the face and forearm of subjects after application of products.

FIG. 17 shows the change in crows' feet (replica) with time after application of products.

FIG. 18 shows the change in crows' feet of subjects after intake of products.

FIGS. 19a-19d show the change in skin elasticity parameters with time after application of products.

FIG. 20 shows the change in skin color brightness with time after application of products.

FIG. 21 shows the change in skin color brightness of subjects after intake of products.

BEST MODE FOR CARRYING OUT INVENTION

Hereinafter, the present disclosure will be described in detail through examples. However, the following examples are for illustrative purposes only and it will be apparent to those of ordinary skill in the art that the scope of the present disclosure is not limited by the examples.

EXAMPLE 1

Preparation of Pomegranate Concentrate through Heating Concentration (1) Preparation of 12NK26

First, 1000 kg of Turkish pomegranate fruits were washed after removing impurities. 450 kg of pomegranate pulp was obtained by cutting the fruits, removing the pericarp and removing the seeds by compression. After filtration, the pomegranate pulp was sterilized at 100-105° C. for 60 seconds and then cooled to 48-55° C. The resulting pomegranate juice was treated with 70-100 mL of pectinase per 1000 L of the juice at 48-55° C. for 1 hour to degrade starches. Then, after adding 900 g of bentonite per 1000 L of the pomegranate juice for maintenance of turbidity and color, provision of viscosity suitable for intake, etc., the mixture was stirred at 48-55° C. for 10 minutes. Then, after vacuum filtration through 1.5-mm and 1-mm filters followed by heating concentration (sequentially, at 70-85° C. and 400-550 mbar up to 12 Brix, at 85-92° C. and 550-750 mbar up to 17 Brix, at 92-100° C. and 750-850 mbar up to 31 Brix, at 60-80° C. and 250-350 mbar up to 43 Brix, and then at 40-60° C. and 100-250 mbar up to 65 Brix), a pomegranate concentrate containing 1.8-3.0 mg/g of ellagic acid and 12.59 mg/g polyphenol (as measured by gallic acid colorimetry) was prepared by filtering through a 0.15-mm filter. The weight ratio of fruit: concentrate in the pomegranate concentrate was 10:1. This pomegranate concentrate was named as sample 12NK26.

(2) Preparation of 12910910

First, Iranian pomegranate fruits were washed after removing impurities. The fruits were cut and the pericarp was removed. The seeds were removed by compressing at 160 bar. After sterilization at low temperature, the resulting pomegranate juice was treated with 100-150 g of pectinase per 6000 L of the juice at 48-60° C. for 1 hour to degrade starches. Then, after adding 1200-1800 g of gelatin, 6000 g of silicon dioxide and 14 kg of bentonite per 6000 L of the pomegranate juice for maintenance of turbidity and color, provision of viscosity suitable for intake, etc., the mixture was stirred at 50-60° C. for 30 minutes. Then, after vacuum filtration followed by heating concentration (sequentially, at 55-90° C. (3 minutes), 105-110° C. (90 seconds) and 100-105° C. (90 seconds)), a pomegranate concentrate containing 0.8-1.4 mg!g of ellagic acid and 11.79 mg/g polyphenol (as measured by gallic acid colorimetry) was prepared. The weight ratio of fruit concentrate in the pomegranate concentrate was 5:1. This pomegranate concentrate was named as sample 12910910.

COMPARATIVE EXAMPLE 1

Preparation of Pomegranate Juice (921217)

First, 1000 kg of Turkish pomegranate fruits were washed after removing impurities. 450 kg of pomegranate pulp was obtained by cutting the fruits, removing the pericarp and removing the seeds by compression. After filtration, the pomegranate pulp was sterilized at 90-94° C. for 20 seconds and then cooled to 15-20° C. As a result, a pomegranate juice containing 0.2-0.32 mg/g of ellagic acid and 0.7-1.55 mg/g polyphenol (as measured by gallic acid colorimetry) was prepared. The weight ratio of fruit concentrate in the pomegranate concentrate was 2:1. This pomegranate juice was named as sample 921217.

EXAMPLE 2

Evaluation of Hyaluronan Synthesis-Promoting Effect of Pomegranate Concentrate

1. Test Materials

Test solutions were prepared by diluting the samples 12NK26, 12910910 and 921217 to concentrations adequate for cell culturing. After conducting preliminary experiments by the WST-1 assay, skin-related effects of the test solutions were evaluated at concentrations not exhibiting cytotoxicity. A positive control group was diluted with a cell culture medium.

TABLE 1

| Reagents and materials | Manufacturer | Catalog No. |
|---|---|---|
| Dulbecco's Modified Eagle's Medium (DMEM) | Welgene | LM-001-01 |
| 48 well plate | SPL | 30048 |
| 96 well plate | SPL | 31096 |
| Cell proliferation reagent WST-1 | Roche | 1644-807 |
| DC protein assay kit | Bio-Rad | 500-0116 |
| Sodium hydroxide (NaOH) | welgene | ML022-02 |
| N-Acetyl-D-glucosamine (NAG) | SIGMA | A8625 |
| Hyaluronan ELISA kit | R&D system | DY3614 |

2. Cell Line and Culturing

Human keratinocytes (HaCaT cells, ATCC) were seeded onto the bottom of a culture dish and cultured at 37° C. in a 5% carbon dioxide incubator after adding Dulbecco's modified Eagle's medium (DMEM, Welgene, Korea) containing penicillin (100 IU/mL), streptomycin (10 μg/mL) and 10% FBS.

3. Cytotoxicity

The cytotoxicity of the test solutions for the HaCaT cells was measured. The HaCaT cells were seeded onto a 96 well plate with $5 \times 10^4$ cells/well and then cultured for 24 hours. Then, after maintaining a starvation state for 12 hours, the test solutions and a fresh medium (without supplements) were added and the cells were cultured for 24 hours. 24 hours later, for measurement of cell survivability, 100 μL of WST-1 solution diluted to 1/10 with a supplement-free medium was treated per well. After incubation for 1 hour, absorbance was measured at 450 nm.

As a result, 12NK26 showed 80% or higher cell survivability at concentrations below 0.5%, 921217 showed 80% or higher cell survivability at concentrations below 1%, and 12910910 showed 80% or higher cell survivability at concentrations below 0.5%.

TABLE 2

| | | (n = 4) |
| Sample | Concentration | % control |
|---|---|---|
| Control | | 100.00 ± 2.125 |
| 12NK26 | 0.05% | 84.06 ± 1.702 |
| | 0.1% | 95.87 ± 5.598 |
| | 0.5% | 83.74 ± 3.854 |
| | 1% | 44.45 ± 1.912 |
| 921217 | 0.1% | 85.11 ± 6.651 |
| | 0.5% | 86.78 ± 5.583 |
| | 1% | 81.01 ± 4.944 |
| | 5% | 75.69 ± 3.727 |
| 12910910 | 0.05% | 87.08 ± 2.575 |
| | 0.1% | 95.13 ± 4.583 |
| | 0.5% | 104.46 ± 4.368 |
| | 1% | 65.02 ± 7.070 |

4. Increase in Hyaluronan Synthesis

The skin-moisturizing effect of the samples was evaluated by measuring the degree of hyaluronan synthesis in keratinocytes by ELISA. For this, the HaCaT cells were seeded onto a plate at $5 \times 10^4$ cells/well and cultured for 24 hours. 24 hours later, the cells were treated with the test samples diluted with the DMEM cell culture medium (without supplements) and cultured for 24 hours. The cultured cells were recovered and the quantity of hyaluronan was measured by hyaluronan ELISA (R&D Systems, DY3614). The cells adherent to the bottom were washed with PBS and lysed with 1 N NaOH to determine the total amount of proteins. Then, the quantity of hyaluronan per given quantity of proteins was calculated.

Measurement of Protein Quantity

The protein quantity was measured using a Bio-Rad DC protein kit according to the Lowry method.

(1) The cell lysate (supernatant) is added to a 96-well plate with 5 μL per well.

(2) Preparation of protein standard 1.5 mg/mL bovine serum albumin (BSA, Bio-Rad, 500-0007) diluted with a cell lysis buffer to 8 different concentrations is added to the 96-well plate with 5 μL per well.

(3) The reagent A and the reagent S included in the kit are mixed at a ratio of 40:1 and added with 25 μL per well.

(4) The reagent B included in the kit is added with 200 μL per well.

(5) After incubation at room temperature for 15 minutes, absorbance is measured at 750 nm.

(6) The total protein quantity is calculated from the BSA calibration curve.

5. Statistics

All data were represented as mean±SD. Statistical analysis was conducted according to the Student's t-test (significance probability p<0.005, two-sided).

6. Result

The effect of the samples 12NK26, 921217 and 129109103 on hyaluronan synthesis was evaluated by ELISA. For this, a hyaluronan ELISA kit (R&D Systems, DY3614) was used. As a result, hyaluronan was measured as 179.6%, 214.4% and 305.1% at concentrations of 0.01%, 0.05% and 0.1% as compared to the control group for 12NK26. The hyaluronan synthesis increased in a concentration-dependent manner. The increase in hyaluronan synthesis was statistically significant at all the three concentrations. For 921217, hyaluronan was measured as 84.0%, 98.3% and 106.2% at concentrations of 0.1%, 0.5% and 1%, respectively, as compared to the control group and no statistical significance was observed at the three concentrations. For 12910910, hyaluronan was measured as 162.4%, 262.4% and 298.2% at concentrations of 0.01%, 0.05% and 0.1% as compared to the control group. The hyaluronan synthesis increased in a concentration-dependent manner. The increase in hyaluronan synthesis was statistically significant at all the three concentrations. For NAG used as a positive control group, 224.8% of hyaluronan was produced when treated with 20 mM as compared to the control group, showing that the hyaluronan biosynthesis by the HaCaT cells is promoted by NAG (see Table 3 and FIG. 2).

TABLE 3

| Sample | Concentration | % control (n = 4) |
| --- | --- | --- |
| Control | | 100.00 ± 20.876 |
| NAG | 20 mM | 224.85 ± 16.937 |
| 12NK26 | 0.01% | 179.66 ± 16.549 |
| | 0.05% | 214.44 ± 13.714 |
| | 0.1% | 305.19 ± 26.122 |
| 921217 | 0.1% | 84.02 ± 17.511 |
| | 0.5% | 98.32 ± 14.297 |
| | 1% | 106.27 ± 19.036 |
| 12910910 | 0.01% | 162.43 ± 6.761 |
| | 0.05% | 262.49 ± 17.319 |
| | 0.1% | 298.27 ± 22.858 |

EXAMPLE 3

Evaluation of Effect of Pomegranate Concentrate on Skin's Physiological Activity 1. Test Materials A test solution was prepared by diluting a pomegranate concentrate (sample 12NK26) prepared as described in Example 1 to a concentration adequate for cell culturing. After conducting preliminary experiments by the WST-1 assay, skin-related effects of the test solution were evaluated at concentrations not exhibiting cytotoxicity. A positive control group was diluted with a cell culture medium.

Other test materials used in this example are as follows.

TABLE 4

| Reagents and materials | Manufacturer | Catalog No. |
| --- | --- | --- |
| Dulbecco's Modified Eagle's Medium (DMEM) | Welgene | LM-001-01 |

TABLE 4-continued

| Reagents and materials | Manufacturer | Catalog No. |
| --- | --- | --- |
| Fibroblast Basal Medium (FBM) | Lonza | CC-3131 |
| 48 well plate | SPL | 30048 |
| 96 well plate | SPL | 31096 |
| Cell proliferation reagent WST-1 | Roche | 1644-807 |
| Procollagen type I c-peptide (PIP) | TAKARA | MK101 |
| DC protein assay kit | Bio-Rad | 500-0116 |
| Sodium hydroxide (NaOH) | welgene | ML022-02 |
| human total MMP-1 ELISA kit | R&D system | DY901 |
| Transforming growth factor-β (TGF-β) | PEPROTECH, INC | 100-21C |
| Retinoic acid | SIGMA | R2625 |
| N-Acetyl-D-glucosamine (NAG) | SIGMA | A8625 |
| Hyaluronan ELISA kit | R&D system | DY3614 |

2. Cell Line and Culturing

For testing of wrinkle improvement, normal human primary dermal fibroblasts, neonatal (HDF-N) derived from the human neonatal foreskin were used. The cells were seeded onto the bottom of a culture dish and cultured at 37° C. in a 5% carbon dioxide incubator after adding the fibroblast basal medium (FBM, Lonza, CC-3131) containing 0.1% insulin, 0.1% rhFGF, 0.1% gentamicin and 2% FBS.

For evaluation of skin-whitening effect, Melan-a cells derived from C57BL/6J (black, a/a) mouse, provided by Dr. Dorothy C Benette (St George's Hospital, London, UK), were used as an immortalized cell line (Bennett D C, Cooper P J, Hart I R. A line of non-tumorigenic mouse melanocyte, syngeneic with the B16 melanoma and requiring a tumor promoter for growth. Int J Cancer 1987; 39: 414-418). The cells were cultured at 37° C. in a 5% carbon dioxide incubator after adding the RPMI 1640 medium containing 10% fetal bovine serum, 50 U/mL penicillin, 50 μg/mL streptomycin, 200 nM phorbol 12-myristate 13-acetate (PMA).

3. Cytotoxicity

The cytotoxicity of the test solutions for the HDF-N cells and Melan-a cells was measured. The HDF-N cells and Melan-a cells were seeded onto a 96 well plate with $6 \times 10^3$ cells/well and $9 \times 10^3$ cells/well, respectively, and then cultured for 24 hours. Then, after maintaining a starvation state for 12 hours, the test solutions and a fresh medium (without supplements or FBS) were added and the cells were cultured for 24 hours. 24 hours later, for measurement of cell survivability, 100 μL of WST-1 solution diluted to 1/10 with a supplement-free medium was treated per well. After incubation for 1 hour, absorbance was measured at 450 nm.

As a result, the pomegranate concentrate sample showed 80% or higher cell survivability at concentrations below 0.1% for the HDF-N cells (Table 5) and 80% or higher cell survivability at concentrations below 0.05% for the Melan-a cells (Table 6).

TABLE 5

| Sample | Concentration | % control (n = 5) |
| --- | --- | --- |
| Control | | 100.00 ± 6.147 |
| Pomegranate concentrate | 0.005% | 93.78 ± 5.175 |
| | 0.01% | 100.42 ± 6.882 |
| | 0.05% | 97.34 ± 4.946 |
| | 0.1% | 94.14 ± 5.402 |
| | 0.5% | 42.67 ± 7.540 |

TABLE 6

| Sample | Concentration | % control (n = 5) |
|---|---|---|
| Control | | 100.00 ± 6.817 |
| Pomegranate concentrate | 0.005% | 107.90 ± 10.084 |
| | 0.01% | 99.70 ± 4.972 |
| | 0.05% | 80.08 ± 8.846 |
| | 0.1% | 68.14 ± 7.841 |

4. Wrinkle-Improving Effect 4-1. Increase in Procollagen

In order to measure the effect of promoting procollagen synthesis of the test solution, HDF-N cells were seeded onto a 48-well plate with $1\times10^4$ cells/well and then cultured for 24 hours. Then, after maintaining a starvation state for 24 hours, the cells were treated with the test solution diluted with the cell culture medium FBM (without supplements) at different concentrations and then cultured for 24 hours. The cultured cells were recovered and the quantity of procollagen was measured using the procollagen type I c-peptide (PIP) EIA kit (Takara, MK101). The cells adherent to the bottom were washed with PBS and lysed with 1 N NaOH to determine the total amount of proteins. Then, the quantity of procollagen per given quantity of proteins was calculated.

As a result, a positive control group treated with 10 ng/mL TGF-β showed 150.8% of procollagen production as compared to the control group. This suggests that the procollagen biosynthesis by the HDF-N cells is promoted by TGF-β. Meanwhile, when the cells were treated with the sample at concentrations of 0.01%, 0.05% and 0.1%, the procollagen production was 96.3%, 53.3% and 53.0%, respectively, and no statistically significant difference from the control group was observed (Table 7).

TABLE 7

| Sample | Concentration | % control (n = 4) |
|---|---|---|
| Control | | 100.00 ± 8.955 |
| TGF-β | 10 ng/ml | 150.88 ± 5.366 |
| Pomegranate concentrate | 0.01% | 96.35 ± 7.440 |
| | 0.05% | 53.36 ± 8.462 |
| | 0.1% | 53.02 ± 4.416 |

4-2. Inhibition of UV-Induced MMP-1 Expression

The effect of the test solution on UV-induced MMP-1 expression was evaluated in order to evaluate the wrinkle-improving effect of the sample by measuring the activity of matrix metalloproteinase (MMP-1) by immuno-ELISA assay. HDF-N cells were seeded onto a 24-well plate with $2\times10^4$ cells/well and then cultured for 24 hours. 24 hours later, after discarding the medium and washing with DPBS, 200 μL of DPBS was added and 5 J/cm$^2$ of UV-A was irradiated. After treating the cells with the sample diluted to an adequate concentration, the cells were cultured for 24 hours. Then, the culture medium was taken and the quantity of MMP-1 was measured with the human total MMP-1 ELISA kit (R&D Systems, DY901). The measured quantity of MMP-1 was calibrated with the total protein quantity.

As a result, the UVA-irradiated group produced 240.2% of MMP-1 as compared to the unirradiated group, which suggests that MMP-1 expression is induced in the HDF-N cells by 5 J/cm$^2$ UVA. Meanwhile, when the HDF-N cells were treated with the pomegranate concentrate at concentrations of 0.001%, 0.005% and 0.01%, the MMP-1 production measured with the human total MMP-1 ELISA kit (R&D Systems, DY901) was 137.1%, 69.3% and 7.1%, respectively, 1 as compared to the UVA-unirradiated group. That is to say, the MMP-1 production decreased in a concentration-dependent manner and the decrease was statistically significant when compared with the UV-irradiated group. Also, retinoic acid used as a positive control group showed 171.6% of MMP-1 production as compared to the UVA-unirradiated group, which was statistically significant decrease as compared to the UV-irradiated group.

TABLE 8

| UV | Sample | Concentration | % UV- (n = 4) |
|---|---|---|---|
| UVA 5 J/cm$^2$ | − | | 100.00 ± 18.728 |
| | + | | 240.25 ± 18.389 |
| | Retinoic acid | 1 μM | 171.68 ± 10.422 |
| | Pomegranate concentrate | 0.0001% | 137.12 ± 21.034 |
| | | 0.0005% | 69.39 ± 12.158 |
| | | 0.001% | 7.11 ± 2.665 |

4-3. Elastase Inhibition Assay

The HDF-N fibroblasts were used to measure the effect of the test solution on elastase activity. For this, the cultured HDF-N cells were treated with 0.2 M Tris-HCl (pH 8.0) containing 0.1% Triton X-100 and lysed by sonication. After centrifuging at 3,000 rpm for 20 minutes and taking the supernatant, the activity of the enzyme was measured by quantifying it and the total protein quantity.

For measurement of the elastase activity, the homogenized fibroblasts were treated with 200 μg/mL elastase, 0.2 M Tris-HCl buffer and the sample at different concentrations. After adding 50 mM STANA, a substrate specific for elastase, and incubating at 37° C., absorbance was measured at 405 nm. The degree of elastase activity inhibition was compared with a control group not treated with the test solution. Phosphoramidon was used as a positive control group.

When absorbance was measured at 405 nm after eating with the pomegranate concentrate at concentrations of 0.05%, 0.1% and 1%, the elastase activity was measured to be 92.3%, 89.5% and 63.6%, respectively, as compared to the control group, showing a decreasing tendency in a concentration-dependent manner. In particular, statistically significant decrease as compared to the control group was observed at all the three concentrations. For the phosphoramidon used as the positive control group, the elastase activity was measured as 74.9% as compared to the control group. The decrease was statistically significant.

TABLE 9

| Sample | Concentration | % control (n = 3) |
|---|---|---|
| Control | | 100.00 ± 0.819 |
| Phosphoramidon | 10 μM | 74.90 ± 5.962 |
| Pomegranate concentrate | 0.05% | 92.31 ± 1.040 |
| | 0.1% | 89.59 ± 3.164 |
| | 1% | 63.65 ± 3.478 |

5. Skin-Whitening Effect 5-1. Tyrosinase Inhibition Assay

A sample solution for measuring tyrosinase activity was prepared by diluting the test solution with ethanol or a suitable solvent to an adequate concentration. After sequentially adding 220 μL of 0.1 M phosphate buffer, 20 μL of the sample solution and 20 μL of a mushroom tyrosinase solution (1500-2000 U/mL) to a test tube, 40 μL of a 1.5 mM tyrosine solution was added to the resulting solution. After incubation at 37° C. for 10-15 minutes, absorbance was measured at 490 nm using the ELISA reader. As a blank solution, 0.1 M phosphate buffer (pH 6.5) was added instead of the sample solution. The sample concentration ($IC_{50}$) when the activity was inhibited by 50% was calculated using a suitable program.

The pomegranate concentrate could not inhibit the tyrosinase activity at concentrations below 0.1%. In contrast, the $IC_{50}$ value of kojic acid used as a positive control group was measured to be 3.634 ppm.

TABLE 10

| Sample | Pomegranate concentrate | Kojic acid |
|---|---|---|
| $IC_{50}$ | — | 3.634 ppm |

(n = 3)

5-2. Inhibition of Melanin Synthesis

Melan-a cells were seeded onto a 24-well plate with $3\times10^4$ cells/well. After culturing the cells in an incubator for 24 hours so that the cells adhered well to the plate, the test solution diluted with a culture medium to different concentrations were added to the respective wells. The test sample was treated once in 3 days, for a total of 6 days. Melanin in the cells was observed with an optical microscope (brightfield microscope). The cells were lysed with 1 N NaOH and then centrifuged. After separating the supernatant, the total amount of proteins was quantified by measuring absorbance at 405 nm. The melanin content was determined from the protein quantity.

As a result, the melanin content was measured as 95.4%, 86.3% and 67.1% when the concentrations of the test solution were 0.005%, 0.01% and 0.05%, respectively, as compared to an untreated control group. That is to say, the melanin synthesis decreased in a concentration-dependent manner and the decrease was statistically significant. When 100 µM arbutin was treated as a positive control group, the melanin synthesis was inhibited in a concentration-dependent manner.

TABLE 11

| Sample | Concentration | % control |
|---|---|---|
| Control | — | 100.00 ± 4.904 |
| Arbutin | 100 µM | 73.54 ± 5.397 |
| Pomegranate concentrate | 0.005% | 95.49 ± 9.277 |
|  | 0.01% | 86.32 ± 1.206 |
|  | 0.05% | 67.12 ± 5.695 |

(n = 4)

6. Statistics

All data were represented as mean±SD. Statistical analysis was conducted according to the Student's t-test (significance probability p<0.005, two-sided).

EXAMPLE 4

Clinical Assessment of Effect of Pomegranate Concentrate on Skin's Physiological Activity

EXAMPLE 4-1

Test Methods

1. Recruitment of Subjects

Test was conducted for 62 female subjects aged between 25 and 60 years who had dry skin, crows' feet and pigmentation. The selected subjects were randomly given a drink containing a pomegranate concentrate (sample 12NK26) prepared according to the method described in Example 1 (test product) or a drink not containing a pomegranate concentrate (control product) and asked to take one pouch a day (50 mL/pouch) for 8 weeks (double-blind test). Before the intake of the test product and at 4 weeks and 8 weeks after the start of the intake, skin-improving effect was evaluated based on visual assessment, skin's water content, skin cornification, TEWL, crows' feet (replica), skin elasticity, skin color brightness (L* value), questionnaire, safety, diet and body weight (including BMI). Also, blood test was conducted before the intake of the test product and at 8 weeks after the start of the intake.

The ingredients included in the drink (test product) containing the pomegranate concentrate (sample 12NK26) and the drink (control product) not containing the pomegranate concentrate and their contents are as follows.

| Ingredients | Test product | Control product | Remarks |
|---|---|---|---|
| Pomegranate concentrate | 10 mL |  | Main ingredient |
| Purified water | 40 mL | 41.5 mL |  |
| Fructooligosaccharide |  | 6.5 mL | Food additive |
| Fructose |  | 1 mL | Food additive |
| Red cabbage color |  | 0.4 mL | Food additive |
| Citric acid |  | 0.5 mL | Food additive |
| Pomegranate flavor |  | 0.1 mL | Food additive |
| Total | 50 mL | 50 mL |  |

2. Measurement and Evaluation

The subjects were divided into a control product group and a test product group through block randomization and the face and left or right forearm were selected as test sites. For the face, measurement was made on the cheek where the corner of the eye meets the tip of the nose (water content, cornification, TEWL, elasticity and skin color), pigmented area (skin color) and Crow's feet (wrinkles). For the inner forearm, measurement was made at the part 5 cm distant from the elbow. The subjects were asked to wash faces and rest for 30 minutes in a space maintained at constant temperature (22±2° C.) and humidity (50±5%) with no air movement and direct sunlight before they participated in the visual assessment, instrumental measurement (skin's water content, cornification, transepidermal water loss, skin elasticity, skin color and crows' feet), survey, body weight (BMI) measurement, dietary investigation and safety evaluation.

3. Visual Assessment

The degree of crows' feet of 2 subjects was evaluated between grades 0 and 9 according to the visual assessment standard of the Guideline for Efficacy Evaluation of Functional Cosmetics II of the Ministry of Korea Food and Drug Safety (July 2005). The wrinkles at the corner of the eye were imaged using the Visia facial imaging system (Canfield Imaging System, USA) in the FL mode.

TABLE 12

| Grade | Description |
|---|---|
| 0 | No skin wrinkle and fine skin texture. |
| 1 | Fine skin wrinkles begin to appear. |
| 2 | Fine skin wrinkles are formed slightly. |
| 3 | There are many fine wrinkles and shallow wrinkles begin to appear. |

TABLE 12-continued

| Grade | Description |
|---|---|
| 4 | Shallow wrinkles are formed slightly. |
| 5 | Shallow wrinkles are distinct but there is no deep wrinkle. |
| 6 | Shallow wrinkles begin to turn to deep wrinkles. |
| 7 | Deep wrinkles are formed slightly. |
| 8 | There are many deep wrinkles. |
| 9 | There are many very deep wrinkles. |

4. Instrumental Measurement

Before the intake of the product and at 4 weeks and 8 weeks after the start of the intake, skin's water content, transepidermal water loss, cornification, skin elasticity and skin color were measured on the left or right cheek of the subjects. Also, left or right crows' feet were measured.

(1) Measurement of skin's water content using Corneometer® CM825

Corneometer® CM825 (Courage+Khazaka GmbH, Germany) measures water content at 30-40 μm beneath the skin's horny layer from capacitance. When current is supplied from a probe, the electrical conductivity of the skin due to the water contained in the skin is displayed in an arbitrary unit (AU). A higher value is measured as the skin's water content is larger. For accurate measurement, measurement was made 3 times for each test sites (cheek, inner forearm) and their mean values were analyzed.

(2) Measurement of Transepidermal Water Loss using Vapometer®

Transepidermal water loss (TEWL) refers to loss of water from the skin and is closely related with the moisturizing function. Because the TEWL value increases as dryness is aggravated, the skin hydration can be evaluated by measuring TEWL. Vapometer® (Delfin, Finland) measures evaporation of water per unit area with time ($g/m^2h$) using temperature and humidity sensors. The evaporation of water at the test sites (cheek, inner forearm) at different times was measured and analyzed.

(3) Measurement of Skin Cornification using D-Squame®

Cornification, which is another measure of skin hydration, is measured by sampling the horny substance from the test sites (cheek, inner forearm) using the D-Squame® black tape. The sample was obtained by attaching the tape on the skin by applying a pressure of 225 $g/cm^2$ for about 5 seconds using the D500 D-Squame® disc applicator and then detaching the tape. The obtained horny substance sample was imaged with Charm View (Moritex, Japan) at 700× magnification and the area was analyzed using the Image-Pro® Plus program.

(4) Measurement of Crows' Feet (Replica) using Visioline® VL-650

Visioline® VL650 (Courage+Khazaka GmbH, Germany) is an instrument which measures the depth, length, etc. of wrinkles in a prepared replica. After mounting the replica on a standard cartridge configured such that a special light passes therethrough, shadow images were obtained using a CCD camera and the maximum wrinkle depth (the depth of the thickest wrinkle) was analyzed.

(5) Measurement of Skin Elasticity using Cutometer®

Skin elasticity is measured using Cutometer® MPA 580 (Courage+Khazaka, Germany). The most frequently used method uses negative pressure and is highly reproducible. The value measured by the Cutometer is between 0 and 1 (mm, ratio). Measurement was made at the test site (front cheek) 3 times for each measurement and the mean values of the parameters (R0-R9) were analyzed. The elasticity parameters were interpreted as follows.

TABLE 13

| Parameters | Description |
|---|---|
| R0 | Highest point of the first curve (skin firmness). |
| R1 | Lowest point of the first curve (ability to return to the skin's original state). |
| R2 | Gross elasticity the closer the value is to 1, the more elastic the skin is). |
| R3 | Highest point of the last curve (tiring effect). |
| R4 | Lowest point of the last curve (tiring effect). |
| R5 | Net elasticity (the closer the value is to 1, the more elastic the skin is). |
| R6 | Portion of viscoelasticity of the curve. |
| R7 | Biological elasticity of the curve. |
| R8 | Ua value of the first curve (the closer Ua and Uf are, the greater is the ability of the skin to return to its original state). |
| R9 | Tiring effect of the skin after repeated sucking in the skin. |

The skin is softer as R0 is higher and firmer as R0 is lower.
The closer R2, R5, R7 and R8 are to 1, the more elastic the skin is.
The lower R1, R3, R4, R6 and R9 are, the more elastic the skin is.

(6) Measurement of Skin Color using Spectrophotometer® CM-700d

Spectrophotometer® CM-700d measures tristimulus values by measuring spectral reflectance and calculates L*, a* and b* values of the CIELAB color system. In the L*a*b* color system, lightness is represented by L* and color and chroma are represented by a* and b*, a* and b* indicate color directions. a* indicates red direction, −a* indicates green direction, b* indicates yellow direction, and −b* indicates blue direction. The color becomes achromatic as the L*, a* and b* values approach 0 and shows high chromaticity in the opposite case. Measurement was made 3 times for each test site (front cheek, pigmented areas) and the skin color lightness (L* value) was averaged.

5. Blood Analysis

The blood of the subjects was examined before the intake of the test product and at 8 weeks after the intake. It was found out that the test product does not affect metabolism.

6. Dietary Investigation and Body Weight Measurement

In order to investigate whether the change in dietary habits of the subjects affected the test result, body weight was measured before the intake of the test product and at 4 and 8 weeks after the start of the intake and dietary investigation was conducted to check whether the dietary habits of the subjects were maintained as usual during the test period. The subjects were asked to self-report given questionnaires on diet.

Diet: (none: 0, little: 1, moderate: 2, much: 3)

7. Survey

The efficacy of the test product and satisfaction at the intake were evaluated before the intake of the test product and at 4 and 8 weeks after the start of the intake based on the questionnaires answered by the subjects.

8. Safety Evaluation

The skin condition of the subjects was examined before the intake of the test product and at 4 and 8 weeks after the start of the intake. Also, the skin condition, systemic condition and irritation by the product were evaluated by interviewing the subjects.

9. Data Analysis

Means and standard deviations (S.D) of the instrumental measurement values were calculated before the intake of the test product and at 4 and 8 weeks after the start of the intake and the difference of the measured values between the measurement times and groups was statistically analyzed. Comparison between the measurement times was conducted by the paired t-test (p<0.05) and comparison between the groups as conducted by the independent t-test (p<0.05). The SPSS® 20.0 program was used for the statistical analysis and the result of survey was analyzed based on frequency.

EXAMPLE 4-2

Test Results

1. Visual Assessment

The crows' feet were decreased (improved) with statistical significance at 8 weeks after the start of the intake of the product (product B) as compared to before the intake of the test product (p<0.05) (Table 14, FIG. 11-12).

TABLE 14

| Group | Week | Mean ± S.D (grade) | p-value† | (n = 62) Change° (%) |
|---|---|---|---|---|
| Product A | Week 0 | 6.05 ± 0.76 | — | — |
|  | Week 4 | 6.03 ± 0.78 | 0.326 | ▼0.33 |
|  | Week 8 | 6.03 ± 0.78 | 0.326 | ▼0.33 |
| Product B | Week 0 | 6.00 ± 0.77 | — | — |
|  | Week 4 | 5.97 ± 0.79 | 0.161 | ▼0.50 |
|  | Week 8 | 5.91 ± 0.79 | 0.032* | ▼1.50 |

†p-value: Paired t-test (*p < 0.05, p < 0.01, *p < 0.001, Significantly different as compared to before the intake of the product.)
°Change: ($W_x$ − W0)/W0 × 100, calculated by mean value.

2. Skin's Water Content

At 4 and 8 weeks after the start of the intake of the product, skin's water content was increased (improved) both on the face and forearm for the test group (product B) as compared to the control group (product A) with statistical significance (p<0.05) (Table 15, FIG. 13).

TABLE 15

| Site | Week | Group | Δ Mean difference ± Std. Error (A.U) | (n = 62) p-value† |
|---|---|---|---|---|
| Face | 4 W | A | −0.04 ± 0.44 | 0.000*** |
|  |  | B | 3.34 ± 0.48 |  |
|  | 8 W | A | 0.86 ± 0.41 | 0.000*** |
|  |  | B | 5.21 ± 0.49 |  |
| Forearm | 4 W | A | 1.00 ± 0.59 | 0.036* |
|  |  | B | 3.16 ± 0.80 |  |
|  | 8 W | A | 2.32 ± 0.64 | 0.013* |
|  |  | B | 4.53 ± 0.57 |  |

†p-value: Independent t-test (*p < 0.05, p < 0.01, *p < 0.001 There is significant difference between the two groups.)

3. Transepidermal Water Loss (TEWL)

At 4 and 8 weeks after the start of the intake of the product, TEWL was decreased (improved) on the forearm for the product B (test group) as compared to the product A (control group) with statistical significance (p<0.05) (Table 16, FIG. 14).

TABLE 16

| Site | Week | Group | Δ Mean difference ± Std. Error (g/m' h) | (n = 62) p-value† |
|---|---|---|---|---|
| Face | 4 W | Product A | −0.29 ± 0.28 | 0.631 |
|  |  | Product B | −0.49 ± 0.29 |  |
|  | 8 W | Product A | −0.86 ± 0.35 | 0.301 |
|  |  | Product B | −1.33 ± 0.28 |  |
| Forearm | 4 W | Product A | 0.05 ± 0.19 | 0.005** |
|  |  | Product B | −0.66 ± 0.16 |  |
|  | 8 W | Product A | −0.39 ± 0.22 | 0.018* |
|  |  | Product B | −1.04 ± 0.16 |  |

†p-value: Independent t-test (*p < 0.05, p < 0.01, *p < 0.001 There is significant difference between the two groups.)

4. Skin Cornification

Skin cornification was decreased (improved) on the face at 4 weeks after the start of the intake of the product and on the face and forearm at 8 weeks after the start of the intake of the product as compared before the intake of the product, with statistical significance (p<0.05). At 8 weeks after the start of the intake of the product, the decrease in skin cornification on the face was 1.84% for the product A (control group) and 6.12% for the product B (test group). On the forearm, the decrease was 0.37% for the product A and 4.09% for the product B (p<0.05) (Table 17).

TABLE 17

| Site | Group | Week | Mean ± S.D (pixel) | p-value† | (n = 62) Change° (%) |
|---|---|---|---|---|---|
| Face | Product A | Week 0 | 230357.50 ± 23015.03 | — | — |
|  |  | Week 4 | 227988.19 ± 23944.58 | 0.454 | ▼1.03 |
|  |  | Week 8 | 226107.52 ± 21733.64 | 0.229 | ▼1.84 |
|  | Product B | Week 0 | 237015.07 ± 24065.03 | — | — |
|  |  | Week 4 | 228910.36 ± 24618.74 | 0.048* | ▼3.42 |
|  |  | Week 8 | 222516.67 ± 20785.20 | 0.000*** | ▼6.12 |
| Forearm | Product A | Week 0 | 249474.38 ± 21609.59 | — | — |
|  |  | Week 4 | 249081.79 ± 22120.34 | 0.806 | ▼0.16 |
|  |  | Week 8 | 248550.90 ± 20482.48 | 0.674 | ▼0.37 |
|  | Product B | Week 0 | 247601.54 ± 20889.48 | — | — |
|  |  | Week 4 | 247391.85 ± 19860.34 | 0.929 | ▼0.08 |
|  |  | Week 8 | 237486.39 ± 19686.42 | 0.003** | ▼4.09 |

†p-value: Paired t-test (*p < 0.05, p < 0.01, *p < 0.001 There is significant difference as compared to before the intake of the product.),
°Change: ($W_x$ − W0)/W0 × 100, calculated by mean value.

At 8 weeks after the start of the intake of the product, the decrease in skin cornification on both the face and forearm was decreased (improved) with statistical significance for the product B as compared to the product A (p<0.05) (Table 18, FIGS. 15-16).

TABLE 18

| Site | Week | Group | Δ Mean difference ± Std. Error (pixel) | (n = 62) p-value† |
|---|---|---|---|---|
| Face | 4 W | Product A | −2369.31 ± 3123.71 | 0.262 |
|  |  | Product B | −8104.71 ± 3928.50 |  |
|  | 8 W | Product A | −4249.98 ± 3457.55 | 0.034* |
|  |  | Product B | −14,498.41 ± 3225.33 |  |
| Forearm | 4 W | Product A | −392.59 ± 1582.37 | 0.949 |
|  |  | Product B | −209.59 ± 2319.13 |  |
|  | 8 W | Product A | −923.48 ± 2172.94 | 0.022* |
|  |  | Product B | −10115.16 ± 3182.20 |  |

†p-value Independent t-test (*p < 0.05, p < 0.01, *p < 0.001 There is significant difference between the two groups.)

5. Crows' Feet (Replica)

At 8 weeks after the start of the intake of the product B (test group), the maximum wrinkle depth was significantly decreased (improved) as compared to before the intake of the product (p<0.05) (Table 19, FIG. 18).

TABLE 19

| Parameters | Group | Week | Mean ± S.D | p-value† | Change° (%) |
|---|---|---|---|---|---|
| Max wrinkle depth (um) | Product A | 0 W | 390.86 ± 93.77 | — | — |
| | | 4 W | 406.59 ± 101.01 | 0.400 | ▲4.02 |
| | | 8 W | 381.14 ± 87.78 | 0.615 | ▼2.49 |
| | Product B | 0 W | 426.16 ± 70.69 | — | — |
| | | 4 W | 420.61 ± 104.50 | 0.756 | ▼1.30 |
| | | 8 W | 391.12 ± 59.42 | 0.021* | ▼8.22 |

†p-value: Paired t-test (*p < 0.05, p < 0.01, *p < 0.001 There is significant difference as compared to before the intake of the product.),
°Change: ($W_x$ − W0)/W0 × 100, calculated by mean value

6. Skin Elasticity

At 8 weeks after the start of the intake of the product, R1 (the ability to return to original state) and R4 (the lowest point of the last curve) were decreased (improved) with statistical significance and R5 (net elasticity) and R7 (biologic elasticity) were significantly increased (improved) for the product B (test group) as compared to the product A (control group). Also, at 4 and 8 weeks after the start of the intake of the product, R2 (gross elasticity) was increased (improved) with statistical significance for the product B as compared to the product A (p<0.05) (Table 20, FIGS. 19a-19d).

TABLE 20

(n = 62)

| Parameters | Week | Group | Δ Mean difference ± Std. Error (mm) | p-value† |
|---|---|---|---|---|
| R0 | 4 W | Product A | 0.0043 ± 0.0056 | 0.890 |
| | | Product B | 0.0030 ± 0.0076 | |
| R0 | 8 W | Product A | −0.0198 ± 0.0068 | 0.420 |
| | | Product B | −0.0271 ± 0.0059 | |
| R1 | 4 W | Product A | 0.0034 ± 0.0020 | 0.060 |
| | | Product B | −0.0045 ± 0.0036 | |
| | 8 W | Product A | −0.0058 ± 0.0032 | 0.002** |
| | | Product B | −0.0199 ± 0.0029 | |
| R2 | 4 W | Product A | −0.0084 ± 0.0031 | 0.001** |
| | | Product B | 0.0186 ± 0.0069 | |
| | 8 W | Product A | −0.0010 ± 0.0065 | 0.000*** |
| | | Product B | 0.0472 ± 0.0071 | |
| R3 | 4 W | Product A | 0.0045 ± 0.0059 | 0.888 |
| | | Product B | 0.0031 ± 0.0080 | |
| | 8 W | Product A | −0.0209 ± 0.0068 | 0.330 |
| | | Product B | −0.0299 ± 0.0061 | |
| R4 | 4 W | Product A | 0.0103 ± 0.0038 | 0.087 |
| | | Product B | −0.0013 ± 0.0054 | |
| | 8 W | Product A | −0.0060 ± 0.0046 | 0.009** |
| | | Product B | −0.0222 ± 0.0040 | |
| R5 | 4 W | Product A | −0.0087 ± 0.0123 | 0.202 |
| | | Product B | 0.0153 ± 0.0138 | |
| | 8 W | Product A | 0.0141 ± 0.0192 | 0.018* |
| | | Product B | 0.0733 ± 0.0150 | |
| R6 | 4 W | Product A | −0.0013 ± 0.0184 | 0.721 |
| | | Product B | 0.0082 ± 0.0187 | |
| | 8 W | Product A | 0.0279 ± 0.0276 | 0.405 |
| | | Product B | 0.0559 ± 0.0194 | |
| R7 | 4 W | Product A | −0.0050 ± 0.0052 | 0.064 |
| | | Product B | 0.0095 ± 0.0057 | |
| | 8 W | Product A | 0.0036 ± 0.0076 | 0.002** |
| | | Product B | 0.0357 ± 0.0062 | |
| R8 | 4 W | Product A | 0.0010 ± 0.0038 | 0.288 |
| | | Product B | 0.0075 ± 0.0047 | |
| | 8 W | Product A | −0.0140 ± 0.0044 | 0.243 |
| | | Product B | −0.0072 ± 0.0037 | |

TABLE 20-continued (n = 62)

| Parameters | Week | Group | Δ Mean difference ± Std. Error (mm) | p-value† |
|---|---|---|---|---|
| R9 | 4 W | Product A | 0.0002 ± 0.0009 | 0.917 |
| | | Product B | 0.0001 ± 0.0010 | |
| | 8 W | Product A | −0.0011 ± 0.0008 | 0.197 |
| | | Product B | −0.0028 ± 0.0011 | |

†p-value: Independent t-test (*p < 0.005, p < 0.01, *p < 0.001 There is significant difference between the two groups.)

7. Skin Color Brightness

Skin color brightness was increased (improved) with statistical significance for the product B (test group) as compared to the product A (control group) on the cheek at 4 weeks after the start of the intake of the product and on both the cheek and pigmented areas at 8 weeks after the start of the intake of the product (p<0.05) (Table 21, FIGS. 20-21).

TABLE 21

(n = 62)

| Site | Week | Group | Δ Mean difference ± Std. Error (L*value) | p-value† |
|---|---|---|---|---|
| Cheek | 4 W | Product A | 0.05 ± 0.06 | 0.025* |
| | | Product B | 0.21 ± 0.04 | |
| | 8 W | Product A | 0.18 ± 0.05 | 0.000*** |
| | | Product B | 0.55 ± 0.07 | |
| Pigmented area | 4 W | Product A | 0.05 ± 0.07 | 0.088 |
| | | Product B | 0.23 ± 0.07 | |
| | 8 W | Product A | 0.17 ± 0.05 | 0.019* |
| | | Product B | 0.40 ± 0.08 | |

†p-value: Independent t-test (*p < 0.05, p < 0.01, *p < 0.001 There is significant difference between the two groups.)

8. Blood Analysis

No statistically significant difference was observed between the two groups in any parameter (p<0.05) (Table 22).

TABLE 22

(n = 62)

| Items | Group | Δ Mean difference ± Std. Error | p-value† |
|---|---|---|---|
| T. Protein | Product A | −0.04 ± 0.06 | 0.089 |
| | Product B | −0.19 ± 0.06 | |
| Albumin | Product A | −0.03 ± 0.04 | 0.929 |
| | Product B | −0.03 ± 0.03 | |
| T. Bil | Product A | 0.03 ± 0.08 | 0.437 |
| | Product B | −0.04 ± 0.04 | |
| SGOT | Product A | 0.10 ± 0.63 | 0.130 |
| | Product B | −1.31 ± 0.67 | |
| SGPT | Product A | 0.40 ± 1.11 | 0.144 |
| | Product B | −1.66 ± 0.86 | |
| T. Chol | Product A | 1.77 ± 3.32 | 0.917 |
| | Product B | 2.25 ± 3.23 | |
| Triglyceride | Product A | −1.90 ± 7.14 | 0.632 |
| | Product B | 2.59 ± 6.09 | |
| Blood sugar (fasting) | Product A | −1.07 ± 1.25 | 0.461 |
| | Product B | −2.25 ± 1.01 | |
| BUN (blood urea nitrogen) | Product A | 0.49 ± 0.66 | 0.534 |
| | Product B | −0.01 ± 0.48 | |
| Creatinine | Product A | 0.01 ± 0.03 | 0.907 |
| | Product B | 0.01 ± 0.02 | |
| Hemoglobin | Product A | −0.29 ± 0.10 | 0.694 |
| | Product B | −0.24 ± 0.09 | |

†p-value: Independent t-test (*p < 0.05, p < 0.01, *p < 0.001 There is significant difference between the two groups.)

9. Dietary Investigation and Body Weight Measurement

There was no significant difference between the two groups in dietary investigation, body weight and BMI for the product A and the product B both before the intake of the product and at 4 and 8 weeks after the start of the intake of the product ($p<0.05$) (Table 23).

TABLE 23

| Items | Group | Week | Mean ± S.D | (n = 62) p-value† |
|---|---|---|---|---|
| Dietary investigation | A | Week 0 | 2.01 ± 0.05 | — |
| | | Week 4 | 2.00 ± 0.04 | 0.786 |
| | | Week 8 | 2.00 ± 0.03 | 0.321 |
| | B | Week 0 | 2.02 ± 0.05 | — |
| | | Week 4 | 2.00 ± 0.04 | 0.200 |
| | | Week 8 | 2.00 ± 0.03 | 0.069 |
| Body weight | A | Week 0 | 57.41 ± 9.44 | — |
| | | Week 4 | 57.60 ± 9.60 | 0.232 |
| | | Week 8 | 57.59 ± 9.71 | 0.328 |
| | B | Week 0 | 57.99 ± 8.33 | — |
| | | Week 4 | 57.75 ± 8.30 | 0.111 |
| | | Week 8 | 57.82 ± 8.32 | 0.266 |
| BMI | A | Week 0 | 22.74 ± 3.72 | — |
| | | Week 4 | 22.86 ± 3.77 | 0.084 |
| | | Week 8 | 22.82 ± 3.74 | 0.354 |
| | B | Week 0 | 23.19 ± 2.75 | — |
| | | Week 4 | 23.15 ± 2.68 | 0.561 |
| | | Week 8 | 23.13 ± 2.71 | 0.367 |

†p-value: Paired t-test (*$p < 0.05$, $p < 0.01$, *$p < 0.001$ There is significant difference as compared to before the intake of the product.)

10. Survey

The satisfaction at the efficacy of the test product was evaluated based on the questionnaires answered by the subjects before the intake of the test product and at 4 and 8 weeks after the start of the intake. The result is as follows (Table 24).

TABLE 24

| | | Product A (n = 30) | | Product B (n = 32) (n = 62) | |
|---|---|---|---|---|---|
| Items | Week | Positive responses (N) | Satisfaction (%) | Positive responses (N) | Satisfaction (%) |
| Improvement of skin moisturization † | 4 W | 6 | 20.00 | 10 | 31.25 |
| | 8 W | 13 | 43.33 | 19 | 59.38 |
| Improvement of skin color † | 4 W | 5 | 16.67 | 8 | 25.00 |
| | 8 W | 15 | 50.00 | 17 | 53.13 |
| Improvement of skin wrinkles † | 4 W | 4 | 13.33 | 7 | 21.88 |
| | 8 W | 9 | 30.00 | 18 | 47.37 |
| 1. Moistness | 4 W | 19 | 63.33 | 17 | 53.13 |
| | 8 W | 21 | 70.00 | 25 | 78.13 |
| 2. Softness | 4 W | 21 | 70.00 | 22 | 68.75 |
| | 8 W | 23 | 76.67 | 28 | 87.50 |
| 3. Decreased tightening | 4 W | 16 | 53.33 | 21 | 65.63 |
| | 8 W | 20 | 66.67 | 22 | 68.75 |
| 4. Reduced cornification | 4 W | 18 | 60.00 | 19 | 59.38 |
| | 8 W | 16 | 53.33 | 18 | 56.25 |
| 5. Fine texture | 4 W | 13 | 43.33 | 18 | 56.25 |
| | 8 W | 18 | 60.00 | 23 | 71.88 |
| 6. Decreased drooping | 4 W | 9 | 30.00 | 17 | 53.13 |
| | 8 W | 10 | 33.33 | 18 | 56.25 |
| 7. Brightened tone | 4 W | 14 | 46.67 | 16 | 50.00 |
| | 8 W | 19 | 63.33 | 24 | 75.00 |
| 8. Healthy skin | 4 W | 17 | 56.67 | 20 | 62.50 |
| | 8 W | 21 | 70.00 | 24 | 75.00 |
| 9. Decreased fine wrinkles | 4 W | 7 | 23.33 | 12 | 37.50 |
| | 8 W | 11 | 36.67 | 14 | 43.75 |

Grades: 0. no change, 1. insignificant, unperceived change, 2. slightly perceived improvement, 3. perceived improvement, 4. distinct improvement-Number (%) of subjects who answered positively: 2-4
Grades: 1. never, 2. no, 3, unlikely, 4. likely, 5. yes, 6. absolutely-Number (%) of subjects who answered positively: 4-6

Grades: 0. no change, 1. insignificant, unperceived change, 2. slightly perceived improvement, 3. perceived improvement, 4. distinct improvement Number (%) of subjects who answered positively: 2-4

Grades: 1, never, 2. no, 3. unlikely, 4. likely, 5, yes, 6. absolutely

Number (%) of subjects who answered positively: 4-6

11. Safety Evaluation

No abnormal response was observed in any subject in dermatological or systemic symptoms throughout the test period (Table 25).

TABLE 25

| | | Product A | | Product B (n = 62) | |
|---|---|---|---|---|---|
| | Symptoms | 4 W | 8 W | 4 W | 8 W |
| Skin | Itchiness | 0 | 0 | 0 | 0 |
| | Pricking pain | 0 | 0 | 0 | 0 |
| | Ticklishness | 0 | 0 | 0 | 0 |
| | Burning | 0 | 0 | 0 | 0 |
| | Stinging | 0 | 0 | 0 | 0 |
| | Stiffness | 0 | 0 | 0 | 0 |
| | Tightness | 0 | 0 | 0 | 0 |
| | Erythema | 0 | 0 | 0 | 0 |
| | Edema | 0 | 0 | 0 | 0 |
| | Cornification | 0 | 0 | 0 | 0 |
| | Pimple | 0 | 0 | 0 | 0 |
| Systemic | Headache | 0 | 0 | 0 | 0 |
| | Dizziness | 0 | 0 | 0 | 0 |
| | Fever | 0 | 0 | 0 | 0 |
| | Lack of appetite | 0 | 0 | 0 | 0 |
| | Sickness | 0 | 0 | 0 | 0 |
| | Vomiting | 0 | 0 | 0 | 0 |
| | Indigestion | 0 | 0 | 0 | 0 |
| | Constipation | 0 | 0 | 0 | 0 |

TABLE 25-continued

| | Product A | | Product B | (n = 62) |
| --- | --- | --- | --- | --- |
| Symptoms | 4 W | 8 W | 4 W | 8 W |
| Diarrhea | 0 | 0 | 0 | 0 |
| Total number of subjects who showed abnormal responses | 0 | 0 | 0 | 0 |

The invention claimed is:

1. A method for promoting hyaluronic acid synthesis, which comprises administering a food or pharmaceutical composition comprising a pomegranate pulp concentrate as an active ingredient to a subject in need of promotion of hyaluronic acid synthesis,
wherein the method provides a skin whitening effect to the subject, and
wherein the pomegranate pulp concentrate comprises 0.8-3 mg/g of ellagic acid and 8-15 mg/g of polyphenol.

2. The method according to claim 1, wherein the subject is a human.

3. The method according to claim 1, wherein the pomegranate pulp concentrate is prepared through a process of treating a pomegranate fruit pulp with a starch-degrading enzyme and then concentrating by heating.

4. The method according to claim 3, wherein the treatment with the starch-degrading enzyme is performed at 40-65° C. within 60 minutes.

5. The method according to claim 3, wherein the concentrating by heating is performed at 40-110° C. for 3 or more times.

6. The method according to claim 5, wherein the concentrating by heating is performed by performing heating concentration at 70-100° C. and 400-850 mbar for 2 or more times and then performing heating concentration at 40-80° C. and 100-350 mbar for 1 or more times.

7. The method according to claim 5, wherein the concentrating by heating is performed by performing first heating concentration at 70-85° C. and 400-550 mbar, performing second heating concentration at 85-92° C. and 550-750 mbar, performing third heating concentration at 92-100° C. and 750-850 mbar, performing fourth heating concentration at 60-80° C. and 250-350 mbar and performing fifth heating concentration at 40-60° C. and 100-250 mbar.

8. The method according to claim 5, wherein the concentrating by heating is performed by performing first heating concentration at 55-90° C., performing second heating concentration at 105-110° C. and performing third heating concentration at 100-105° C.

9. The method according to claim 1, wherein the food composition is in the form of a fortified food, a dietary supplement, a non-alcoholic drink, a sports drink, a fruit drink, tea-or milk-based drink or a liquid food.

10. The method according to claim 1, wherein the method is effective for improving skin moisturization.

11. The method according to claim 1, wherein the method has an effect of inhibiting melanin synthesis.

12. The method according to claim 1, wherein the method has one or more effects selected from the group consisting of improvement of skin moisturization, improvement of wrinkles, improvement of skin elasticity and reduction of cornification.

* * * * *